(12) United States Patent
Chen et al.

(10) Patent No.: US 8,030,304 B2
(45) Date of Patent: Oct. 4, 2011

(54) THIAZOLE PYRAZOLOPYRIMIDINES CRF1 RECEPTOR ANTAGONISTS

(75) Inventors: Zhaogen Chen, Indianapolis, IN (US); Chafiq Hamdouchi Hamdouchi, Carmel, IN (US); Erik James Hembre, Indianapolis, IN (US); Philip Arthur Hipskind, New Palestine, IN (US); Jason Kenneth Myers, Indianapolis, IN (US); Takako Takakuwa, Indianapolis, IN (US); James Lee Toth, Knightstown, IN (US)

(73) Assignee: Eli Lilly and Company, Indianapolis, IN (US)

( * ) Notice: Subject to any disclaimer, the term of this patent is extended or adjusted under 35 U.S.C. 154(b) by 287 days.

(21) Appl. No.: 12/377,733

(22) PCT Filed: Sep. 17, 2007

(86) PCT No.: PCT/US2007/078605
§ 371 (c)(1),
(2), (4) Date: Feb. 17, 2009

(87) PCT Pub. No.: WO2008/036579
PCT Pub. Date: Mar. 27, 2008

(65) Prior Publication Data
US 2010/0222339 A1    Sep. 2, 2010

Related U.S. Application Data

(60) Provisional application No. 60/826,264, filed on Sep. 20, 2006.

(51) Int. Cl.
| | |
|---|---|
| *A01N 43/58* | (2006.01) |
| *A01N 43/54* | (2006.01) |
| *A01N 43/64* | (2006.01) |
| *A01N 43/78* | (2006.01) |
| *A01N 43/56* | (2006.01) |
| *A61K 31/50* | (2006.01) |
| *A61K 31/505* | (2006.01) |
| *A61K 31/41* | (2006.01) |
| *A61K 31/425* | (2006.01) |
| *A61K 31/415* | (2006.01) |
| *C07D 239/42* | (2006.01) |
| *C07D 401/04* | (2006.01) |
| *C07D 471/04* | (2006.01) |
| *C07D 471/22* | (2006.01) |
| *C07D 487/04* | (2006.01) |

(52) U.S. Cl. ........ 514/247; 514/256; 514/257; 514/267; 514/359; 514/365; 514/366; 514/403

(58) Field of Classification Search .................. 514/247, 514/256, 257, 267, 359, 365, 366, 403
See application file for complete search history.

(56) References Cited

FOREIGN PATENT DOCUMENTS

| | | |
|---|---|---|
| WO | 94/13676 | 6/1994 |
| WO | WO 94/13676 | 6/1994 |
| WO | WO 97/29109 | 8/1997 |
| WO | WO 98/03510 | 1/1998 |
| WO | 98/08847 | 3/1998 |
| WO | WO 98/08847 | 3/1998 |
| WO | WO 00/59908 | 10/2000 |
| WO | WO 01/23388 | 4/2001 |
| WO | WO 02/072202 | 9/2002 |
| WO | WO 2005/063755 | 7/2005 |

OTHER PUBLICATIONS

Gehlert, et al.,"3-(4-Chloro-2morpholin-4-yl-thiazol-5-y1)-8-(1-ethylpropy1)-2,6-dimethyl-imidazo[1,2-b]pyridazine : a novel brain-penetrant, orally available corticotropin-releasing factor receptor 1 antagonist with efficacy in animal models of alcoholism", *The J. Of Neuroscience*, vol. 27(10)27-18-2726 (2007).
He Liqi, et al., "4-(1,3-Dimethoxyprop-2-ylamino)-2,7-dimethyl-8-(2,4-dichlorophenyl)pyrazolo[1,5-a]-1,3,5-triazine: A Potent, Orally Bioavailable CRF1 Receptor Antagonist" *J. Of Medicinal Chem. American Chem. Society*. Washington, US, vol. 43, 449-456, XP002196777 (2000).
Chen, et al., Design of 2,5-Dimethyl-3-(6-dimethyl-4-methylpyridin-3-yl)-7-dipropyl aminopryazolo[1,5-a]pyrimidine (NBI 30775/R121919) and Structure-Activity Relationships of a Series of Potent and Orally Active Corticotropin- Releasing Factor Receptor Antagonists', J. O Medicinal Chemistry Society. Washington, US .47(19) 4787-4798, XP001206057 (2004).
Gilligan, P., et al., <<The Discovery of 4-(3-Pentylamino)-2,7-dimethyl-8-(2-methyl-4-methoxyphenyl)-pyrazolo-[1,5-α]-pyrimidine: A corticotrophin-Releasing Factor (hCRF1)Antagonist; *Bioorganic & Medicinal Chemistry* 8, 181-189 (2000).

*Primary Examiner* — Yong Chong
(74) *Attorney, Agent, or Firm* — R. Craig Tucker

(57) ABSTRACT

The present invention relates to compounds of Formula (I), pharmaceutical compositions thereof, and use thereof as corticotropin releasing factor 1 (CRF1) receptor antagonists in the treatment of psychiatric and neuroendocrine disorders, neurological diseases, and metabolic syndrome.

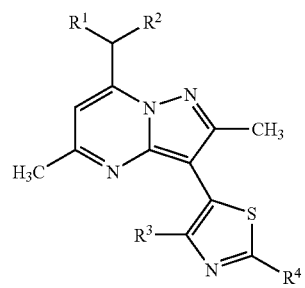

10 Claims, No Drawings

THIAZOLE PYRAZOLOPYRIMIDINES CRF1 RECEPTOR ANTAGONISTS

This U.S. national stage application of International Application PCT/US2007/078605, filed 17 Sep. 2007, claims priority to U.S. provisional application Ser. No. 60/826,264, filed 20 Sep. 2006.

FIELD OF THE INVENTION

This invention relates to novel thiazole pyrazolopyrimidine compounds, pharmaceutical compositions thereof, and use thereof as CRF1 receptor antagonists in the treatment of psychiatric and neuroendocrine disorders, neurological diseases, and metabolic syndrome.

BACKGROUND OF THE INVENTION

Corticotropin releasing factor (CRF) is a 41 amino acid peptide that is the primary physiological regulator of proopiomelanocortin (POMC) derived peptide secretion from the anterior pituitary gland. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in the brain. There is also evidence that CRF plays a significant role in integrating the response in the immune system to physiological, psychological, and immunological stressors.

CRF has been implicated in psychiatric disorders and neurological diseases including depression and anxiety, as well as the following: Alzheimer's disease, Huntington's disease, progressive supranuclear palsy, amyotrophic lateral sclerosis, Parkinson's disease, epilepsy, migraine, alcohol and substance abuse and associated withdrawal symptoms, obesity, metabolic syndrome, congenital adrenal hyperplasia, Cushing's disease, hypertension, stroke, irritable bowel syndrome, stress-induced gastric ulceration, premenstrual syndrome, sexual dysfunction, premature labor, inflammatory disorders, allergies, multiple sclerosis, visceral pain, sleep disorders, pituitary tumors or ectopic pituitary-derived tumors, chronic fatigue syndrome and fibromyalgia.

CRF receptor subtypes, CRF1 and CRF2, have been identified and are distributed heterogeneously within the brain thereby suggesting potential functional diversity. For example, widely distributed brain CRF1 receptors are strongly implicated in emotionality accompanying exposure to environmental stressors. Significantly, CRF1, not CRF2, receptors appear to mediate select anxiogenic like behaviors. A more discrete septal/hypothalmic distribution and the availability of alternative endogenous ligands suggest a different functional role for the CRF2 receptor. For example, a novel CRF-family neuropeptide with preferential affinity for CRF2 relative to CRF1 receptors is reported to suppress appetite without producing the profile of behavioral activation observed with selective CRF1 agonism. In other cases, CRF2 agonism produces similar effects to those reported for CRF1 antagonists or CRF1 gene deletion. For example, while CRF2 agonists have been proposed as antiobesity agents, CRF1 antagonists may be an important treatment for obesity as well.

Certain pyrrolo[2,3-d]pyrimidines, pyrrolo[3,2-d]pyrimidines, pyrazolo[1,5-a]pyrimidines, 1,2,3-triazolo[4,5-b]pyridines, and pyrazolo[1,5-a]-1,3,5-triazines, useful as CRF antagonists, are described in WO 94/13676, WO 97/29109, WO 98/08847, and WO 98/03510.

The present invention provides novel thiazole pyrazolopyrimidines useful as CRF1 receptor antagonists. In view of the above, it is desirable to discover new efficacious and selective antagonists of CRF1 as potentially valuable therapeutic agents for the treatment of psychiatric and neuroendocrine disorders, neurological diseases, and metabolic syndrome. Further, since a majority of commercial CNS and cardiovascular drugs exhibit unfavorable bioavailability and pharmacokinetic profiles, it is also desirable to discover new compounds with favorable bioavailability and pharmacokinetic profiles relative to known CRF antagonists such as CP154526 and NBI30775.

SUMMARY OF THE INVENTION

In one embodiment, the present invention provides a compound of Formula I

Formula I

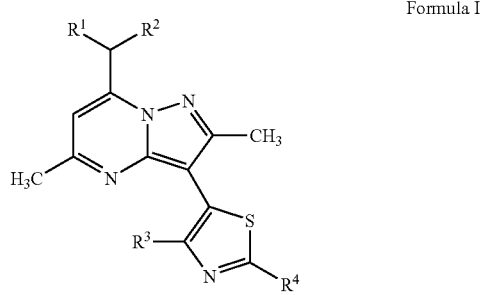

wherein:
$R^1$ and $R^2$ are independently ethyl or n-propyl;
$R^3$ is hydrogen, Cl, Br, methyl, trifluoromethyl or methoxy;
$R^4$ is hydrogen, Br, $R^aR^bN-$, methoxymethyl, n-butyl, acetamido, pyridin-4-yl, morpholin-4-yl,

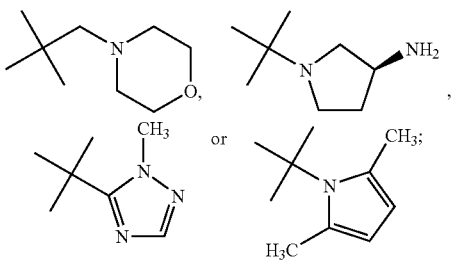

$R^a$ and $R^b$ are independently hydrogen, $C_1$-$C_3$alkyl, $H_2NCH_2CH_2-$, $(CH_3)_3COC(O)NHCH_2CH_2-$, or $CH_3CH_2CH_2NHCH_2CH_2-$;
or a pharmaceutically acceptable salt thereof In another embodiment, the present invention provides a pharmaceutical composition comprising: a compound of Formula I, or a pharmaceutically acceptable salt thereof, and a pharmaceutically acceptable excipient.

In another embodiment, the present invention relates to a method of treating depression, anxiety, alcohol or substance abuse, obesity, hypertension, metabolic syndrome, irritable bowel syndrome, epilepsy, stroke, sleep disorders, allergy, migraine, premenstrual syndrome, infertility, sexual dysfunction, congenital adrenal hyperplasia, Cushing's disease, premature labor, stress-induced gastric ulceration, inflammatory disorders, pituitary or ectopic pituitary-derived tumors, chronic fatigue syndrome, fibromyalgia, visceral pain or multiple sclerosis in a patient, comprising: administering to a patient in need thereof a therapeutically effective amount of a compound of Formula I, or a pharmaceutically acceptable salt thereof.

In another embodiment, the present invention relates to use of a compound of Formula I, or a pharmaceutically acceptable salt thereof, for the manufacture of a medicament for the treatment of depression, anxiety, alcohol or substance abuse, obesity, hypertension, metabolic syndrome, irritable bowel syndrome, epilepsy, stroke, sleep disorders, allergy, migraine, premenstrual syndrome, infertility, sexual dysfunction, congenital adrenal hyperplasia, Cushing's disease, premature labor, stress-induced gastric ulceration, inflammatory disorders, pituitary or ectopic pituitary-derived tumors, chronic fatigue syndrome, fibromyalgia, visceral pain or multiple sclerosis.

In another embodiment, the present invention relates to a compound of Formula I, or a pharmaceutically acceptable salt thereof, for use in the treatment of depression, anxiety, alcohol or substance abuse, obesity, hypertension, metabolic syndrome, irritable bowel syndrome, epilepsy, stroke, sleep disorders, allergy, migraine, premenstrual syndrome, infertility, sexual dysfunction, congenital adrenal hyperplasia, Cushing's disease, premature labor, stress-induced gastric ulceration, inflammatory disorders, pituitary or ectopic pituitary-derived tumors, chronic fatigue syndrome, fibromyalgia, visceral pain or multiple sclerosis.

In another embodiment, the present invention relates to a compound of Formula I, or a pharmaceutically acceptable salt thereof, for use in therapy.

DETAILED DESCRIPTION OF THE INVENTION

As used above, and throughout the description of the invention, the following terms, unless otherwise indicated, shall be understood to have the following meanings:

"Alkyl" means a saturated aliphatic hydrocarbon group, which may be straight or branched, having 1 to 5 carbon atoms in the chain.

"Pharmaceutically acceptable excipient" refers to a pharmaceutically acceptable formulation carrier, solution, or additive to enhance the formulation characteristics. Such excipients must be compatible with the other ingredients of the formulation and not deleterious to the recipient thereof and are well known to the skilled artisan (see e.g. *Remingtons Pharmaceutical Sciences*, 19$^{th}$ Edition, Mack Publishing Company, 1995).

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed (see e.g. *Remingtons Pharmaceutical Sciences*, 19$^{th}$ Edition, Mack Publishing Company, 1995).

"Therapeutically effective amount" or "effective amount" means the amount of the compound of formula I of the present invention or pharmaceutical composition containing a compound of formula I of the present invention that will elicit the biological or medical response of or desired therapeutic effect on a tissue, system, animal or human that is being sought by the researcher, veterinarian, medical doctor or other clinician.

The terms "treatment," "treat," "treating," and the like, are meant to include both slowing and reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed. The term "treatment" and like terms also include preventive (e.g., prophylactic) and palliative treatment. Prevention of the disease is manifested by a prolonging or delaying of the onset of the symptoms of the disease.

The symbol "—" in a molecular structure indicates the position of attachment for that particular substituent.

When any variable occurs more than one time in any constituent or in formula I, its definition on each occurrence is independent of its definition at every other occurrence. Also, combinations of substituents and/or variables are permissible only if such combinations result in stable compounds. In choosing compounds of the present invention, one of ordinary skill in the art will recognize that the various substituents, i.e. $R^1$, $R^2$, etc., are to be chosen in conformity with well-known principles of chemical structure connectivity.

Under standard nomenclature used throughout this disclosure, the terminal portion of the designated side chain is described first, followed by the adjacent functionality toward the point of attachment. For example, an arylcarbonylaminoalkyl substituent is equivalent to aryl-C(O)—NH-alkyl-.

The present invention contemplates the following embodiments, which can alternatively be further combined:

(a) A compound of Formula I wherein $R^1$ and $R^2$ are ethyl;
(b) A compound of Formula I wherein $R^1$ and $R^2$ are n-propyl;
(c) A compound of Formula I wherein $R^3$ is Cl, Br, methyl or trifluoromethyl;
(d) A compound of Formula I wherein $R^3$ is Cl;
(e) A compound of Formula I wherein $R^3$ is Br;
(f) A compound of Formula I wherein $R^4$ is $R^aR^bN$—, pyridin-4-yl, morpholin-4-yl, or

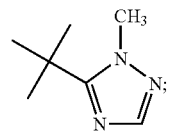

(g) A compound of Formula I wherein $R^4$ is morpholin-4-yl;
(h) A compound of Formula I wherein $R^4$ is

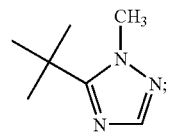

(i) A compound of Formula I wherein $R^a$ and $R^b$ are independently $C_1$-$C_3$alkyl;
(j) A compound of Formula I wherein $R^1$ and $R^2$ are ethyl, $R^3$ is Cl, and $R^4$ is morpholin-4-yl;
(k) A compound of Formula I wherein $R^1$ and $R^2$ are n-propyl, $R^3$ is Cl, and $R^4$ is morpholin-4-yl;
(l) A compound of Formula I wherein $R^1$ and $R^2$ are ethyl, $R^3$ is Br, and $R^4$ is morpholin-4-yl;
(m) A compound of Formula I wherein $R^1$ and $R^2$ are n-propyl, $R^3$ is Br, and $R^4$ is morpholin-4-yl;
(n) A compound of Formula I wherein $R^1$ and $R^2$ are ethyl, $R^3$ is Cl, and $R^4$ is

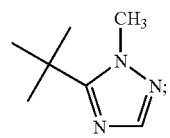

(o) A compound of Formula I wherein $R^1$ and $R^2$ are n-propyl, $R^3$ is Cl, and $R^4$ is

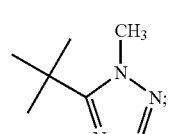

(p) A compound of Formula I wherein $R^1$ and $R^2$ are ethyl, $R^3$ is Br, and $R^4$ is

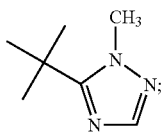

(q) A compound of Formula I wherein $R^1$ and $R^2$ are n-propyl, $R^3$ is Br, and $R^4$ is

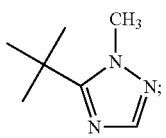

(r) Use of a compound of Formula I, or a pharmaceutically acceptable salt thereof, for treating depression or anxiety;
(s) Use of a compound of Formula I, or a pharmaceutically acceptable salt thereof, for treating alcohol or substance abuse;
(t) Use of a compound of Formula I, or a pharmaceutically acceptable salt thereof, for treating alcohol or substance abuse and associated withdrawal symptoms;
(u) A compound of Formula I, or a pharmaceutically acceptable salt thereof, exhibiting a Ki value for CRF1 binding of ≦500 nM;
(v) A compound of Formula I, or a pharmaceutically acceptable salt thereof, exhibiting a Ki value for CRF1 binding of ≦50 nM;
(w) A compound of Formula I, or a pharmaceutically acceptable salt thereof, exhibiting a Ki value for CRF1 binding of ≦5 nM;
(x) A compound of Formula I, or a pharmaceutically acceptable salt thereof, exhibiting a Ki value for CRF1 binding of 500 nM and selectively binding to CRF1 (i.e., lower Ki) relative to CRF2;
(y) A compound of Formula I, or a pharmaceutically acceptable salt thereof, exhibiting a Ki value for CRF1 binding of ≦50 nM and selectively binding to CRF1 (i.e., lower Ki) relative to CRF2;
(z) A compound of Formula I, or a pharmaceutically acceptable salt thereof, exhibiting a Ki value for CRF1 binding of ≦5 nM and selectively binding to CRF1 (i.e., lower Ki) relative to CRF2; and/or
(aa) Particular exemplified compounds with superior bioavailability and pharmacokinetic profiles relative to some known CRF antagonists (e.g., CP154526 and NBI30775), such as Example 15.

The compounds of the present invention are preferably formulated as pharmaceutical compositions administered by a variety of routes. Preferably, such compositions are for oral administration. Such pharmaceutical compositions and processes for preparing same are well known in the art (see, e.g., Remington: The Science and Practice of Pharmacy, A. Gennaro, et al., eds., 19th ed., Mack Publishing Co., 1995).

The compounds of Formula I are generally effective over a wide dosage range. For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

The compounds of Formula I are CRF-1 antagonists and, as such, are useful for treating a condition which is treatable by reducing CRF1 receptor tone or stimulation.

Corticotropin releasing factor (CRF), a 41 amino acid peptide that is the primary physiological regulator of proopiomelanocortin (POMC) derived peptide secretion from the anterior pituitary gland [J. Rivier et al., Proc. Natl. Acad. Sci (USA) 80:4851 (1983); W. Vale et al., Science 213:1394 (1981)], has been linked to a number of medical conditions. For example, in addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in the brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985) ]. There is also evidence that CRF plays a significant role in integrating the response in the immune system to physiological, psychological, and immunological stressors [see, e.g., J. E. Blalock, Physiological Reviews 69:1 (1989); J. E. Morley, Life Sci. 41:527 (1987)].

CRF is involved in psychiatric disorders and neurological diseases including depression and anxiety [D. M. Nielsen, Life Sci. 78:909-919; H. E. Kunzel et al., J. Psychiatr. Res. 37:525-533; D. R. Gehlert et al., Eur. J. Pharmacol. 509:145-153]. A role for CRF has also been postulated in the etiology and pathophysiology of Alzheimer's disease, Huntington's disease, progressive supranuclear palsy and amyotrophic lateral sclerosis, as they relate to the dysfunction of CRF neurons in the central nervous system [for a review, see: E. B. De Souze, Hosp. Practice 23:59 (1988)]. Chronic administration of CRF has been shown to produce impairment of the dopamine system suggesting a role in Parkinson's disease [E. Izzo et al., Pharmacol. Biochem. Behav. 81:701-708 (2005)]. Other neurological disorders in which CRF is involved include epilepsy [T. Z. Baram et al., Brain Res. 770:89-95 (1997)] and migraine [T. C. Theoharides et al., Endocrinology 136:5745-5750 (1995)]. CRF has been implicated in alcohol and substance abuse and associated withdrawal symptoms [D. H. Overstreet et al., Pharmacol. Biochem. Behav. 77:405-413; Y. Shaham et al., Psychopharmacology (Berl) 137:184-190]. Moreover, there is evidence that CRF has a role in various endocrine disorders and cardiovascular diseases such as obesity [E. Timofeeva and D. Richard, Neuroendocrinology 66:327-340 (1997)], metabolic syndrome [A. M. Ward et al., Metabolism 53:720-726(2004)], congenital adrenal hyperplasia [D. P. Merke and G. B. Cutler Jr., Endocrinol. Metab. Clin. North Am. 30:121-135 (2001)], Cushing's disease [M. Labeur et al., Curr. Drug Targets Immune Endocr. Metabol. Disord. 4:335-342 (2004)], hypertension [R. J. Briscoe, et al., Brain Res. 881:204-207 (2000)], and stroke [S. L. Stevens et al., J. Cereb. Blood Flow Metab. 23:1151-1159 (2003)]. Gastric disturbances such as irritable bowel syndrome [Y. Tache et al., Eur J. Surg. Suppl 1:16-22 (2002)] and stress-induced gastric ulceration [K. E. Gabry et al., Mol. Psychiatry 7:474-

483, 433 (2002)] have been shown to be related to CRF. In addition, there is indication that CRF has a role in various areas of human female health, for example, premenstrual syndrome [F. Facchinetti et al., *Psychosom. Med.* 56:418-422 (1994)], infertility [L. Ghizzoni et al., *Endocrinology* 138: 4806-4811 (1997)], sexual dysfunction [J. E. Jones et al., *Am. J. Physiol. Regul. Integr. Comp. Physiol.* 283:R591-597 (2002)], and premature labor [P. D. Wadhwa et al., *Am. J. Obstet. Gynecol.* 191:1063-1069 (2004)]. There is also evidence that CRF has a significant role in the immune system indicating therapeutic potential for treating inflammatory disorders [A. Gravanis and A. N. Margioris, *Curr. Med. Chem.* 12:1503-1512 (2005)], allergies [L. K. Singh et. al., *Brain Behav. Immun.* 13:225-239 (1999)], multiple sclerosis and other autoimmune disorders [C. Benou et al., *J. Immunol.* 174:5407-5413 (2005)]. In addition to the preceding, CRF has been implicated in visceral pain [M. Nijsen et al., *Neurogastroenterol. Motil.* 17:423-432 (2005)], sleep disorders [T. M. Buckley and A. F. Schatzberg, *J. Clin. Endocrinol. Metab.* 90:3106-3114(2005)], pituitary tumors or ectopic pituitary-derived tumors [K. D. Dieterich et al., *J. Clin. Endocrinol. Metab.* 83:3327-3331 (1998)], chronic fatigue syndrome and fibromyalgia [G. Neeck and L. J. Crofford, *Rheum. Dis. Clin. North Am.* 26:989-1002 (2000)].

CRF receptor subtypes, CRF1 and CRF2, have been identified and are distributed heterogeneously within the brain [D. T. Chalmers et al., *TIPS* 17:166-72 (1996)] thereby suggesting potential functional diversity [S. C. Heinrichs et al., *Regul. Peptides* 71:15 (1997)]. For example, widely distributed brain CRF1 receptors are strongly implicated in emotionality accompanying exposure to environmental stressors [G. Liebsch et al., *Regul. Peptides* 59: 229-39 (1995); D. W. Schulz, *PNAS* 93: 10477-82 (1996)]. Significantly, CRF1, not CRF2, receptors appear to mediate select anxiogenic like behaviors [Heinrichs et al., 1997]. A more discrete septal/hypothalmic distribution [D. T. Chalmers et al., *J. Neurosci.* 15(10): 6340-50 (1995)] and the availability of alternative endogenous ligands [J. Vaughan et al., *Nature* 378: 287-92 (1995)] suggest a different functional role for the CRF2 receptor [Heinrichs et al., 1997]. For example, a novel CRF-family neuropeptide with preferential affinity for CRF2 relative to CRF1 receptors is reported to suppress appetite without producing the profile of behavioral activation observed with selective CRF1 agonism (H. Tezval et al., *PNAS* 101 (25): 9468-9473 (2004)]. In some cases, CRF2 agonism produces similar effects to those reported for CRF1 antagonists or CRF1 gene deletion [S. C. Heinrichs, *Trends in Pharmacological Sciences* 20(8):311-5 (1999)]. For example, while CRF2 agonists have been proposed as antiobesity agents, CRF1 antagonists may be an important treatment for obesity as well [C. Contoreggi et al., *Neuroendocrinology* 80(2):111-23 (2004)].

PREPARING COMPOUNDS OF THE INVENTION

All of the compounds of the present invention can be chemically prepared, for example, by following the synthetic routes set forth below. However, the following discussion is not intended to be limiting to the scope of the present invention in any way. For example, the specific synthetic steps for each of the routes described may be combined in different ways, or in conjunction with steps from different schemes, to prepare additional compounds of Formula I. The products of each step can be recovered by conventional methods including extraction, evaporation, precipitation, chromatography, filtration, trituration, crystallization, and the like. In the Schemes below all substituents, unless otherwise indicated, are as previously defined and suitable reagents are well known and appreciated in the art.

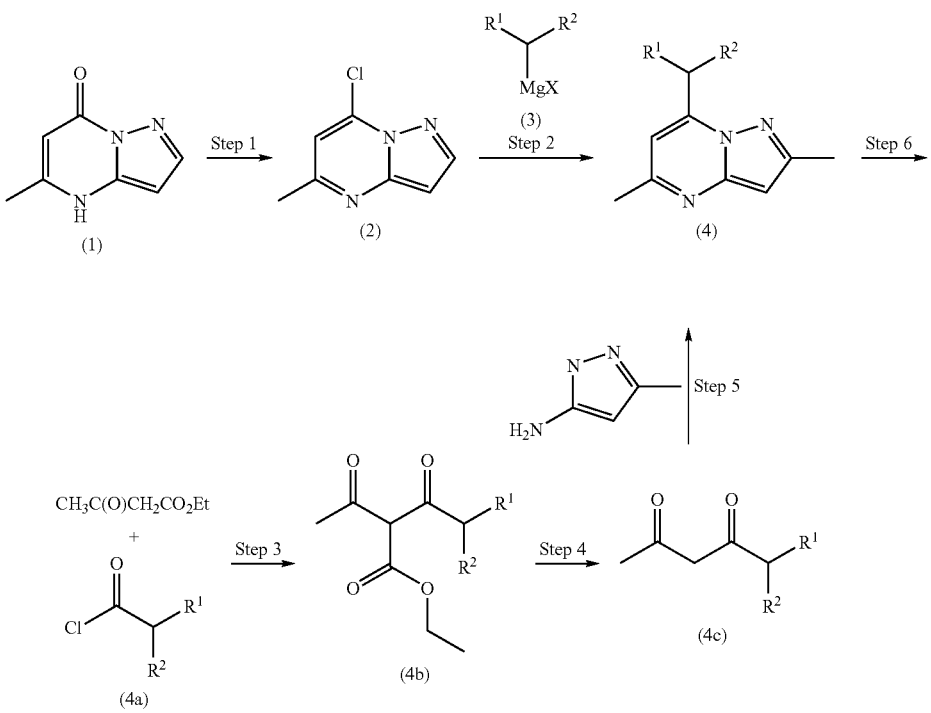

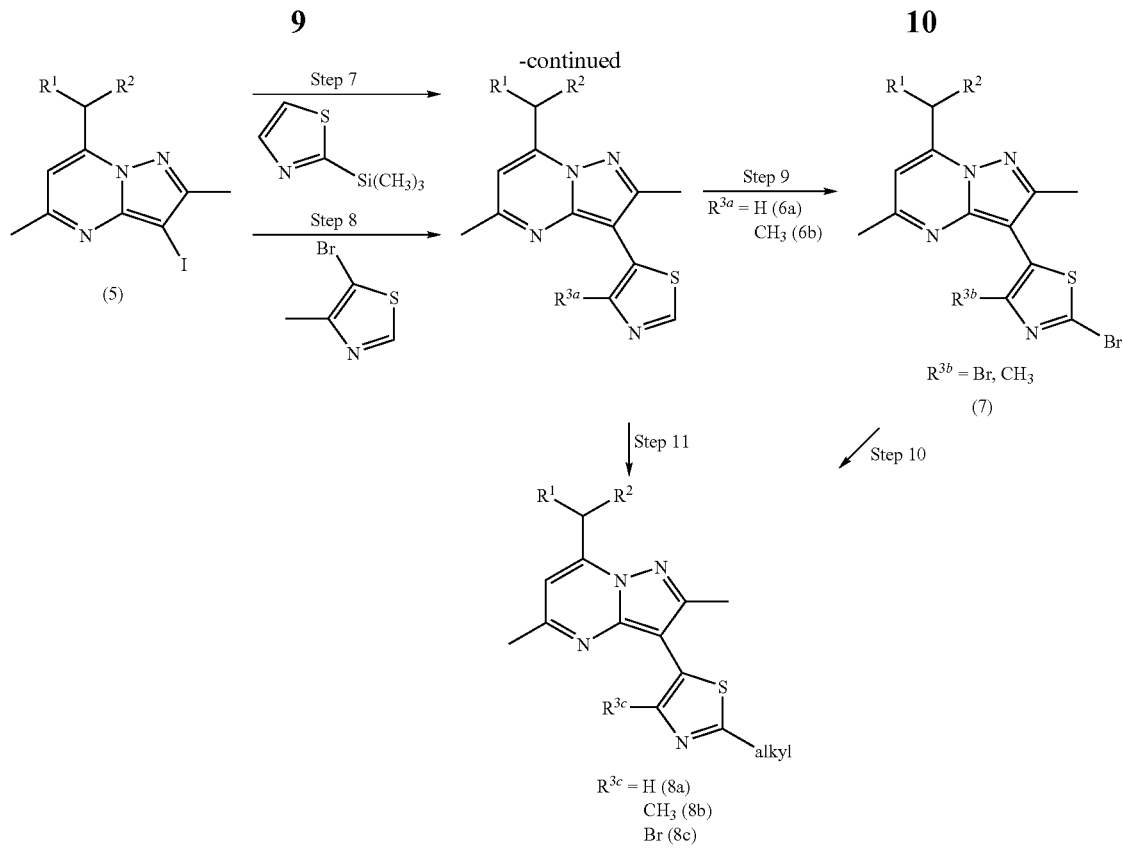

Formation of a compound of formula (6a,b), (7), or 8(a-c) can be carried out in accordance with reactions as depicted in Scheme 1. An appropriate compound of formula (6a,b), (7), or (8a-c) is one in which $R^1$ and R are as defined for formula I and $R^{3a}$=H or $CH_3$, $R^{ab}$=Br or $CH_3$ and $R^{3c}$=H, $CH_3$, or Br.

In Scheme 1, Step 1, the pyrazolo[1,5-a]pyrimidine-7-one of formula (1) is converted to 7-chloro-2,5-dimethyl- pyrazolo[1,5-a]pyrimidine using phosphorous oxychloride and dimethylaniline in an inert solvent, such as toluene, at the reflux temperature of the solvent.

In Step 2, a Grignard reagent of formula (3) (X=Cl or Br) is reacted with the chloride of formula (2), in an inert solvent such as toluene, at reflux temperature to provide the 7-alkyl pyrazolopyrimidine of formula (4).

Alternatively, a 7-alkyl pyrazolopyrimidine of formula (4) can be obtained as shown in Steps 3, 4, and 5. In Step 3 ethyl acetoacetate is acylated with an acid halide of formula (4a) in the presence of magnesium chloride to provide a diketo-ester of formula (4b). The diketo-ester of formula (4b) is decarboxylated under Krapcho conditions to provide the diketone of formula (4c). For example, (4b) is heated in dimethyl sulfoxide at a temperature of about 130 to 170° C. to perform the decarboxylation. In Step 5, the diketone of formula (4c) is cyclized with 3-amino-5-methylpyrazole to give the 7-alkyl pyrazolopyrimidine of formula (4) in a protic solvent such as methanol, ethanol, or acetic acid. Preferred conditions use acetic acid at a temperature of about 0 to 60° C.

The pyrazolopyrimidine of formula (4) is functionalized to an iodo pyrazolopyrimidine of formula (5) in Step 6 using an excess of N-iodosuccinimide in acetonitrile.

In Scheme 1, Step 7 or 8, the iodo pyrazolopyrimidine of formula (5) is reacted with a thiazole zinc halide in a Negishi cross-coupling reaction to provide a thiazolyl pyrazolopyrimidine of formula (6a) or (6b) (Jensen, J.; Skjaerbaek, N.; Vedso, P. Synthesis 2001, 128). The thiazole zinc halide is generated using methods well known to those skilled in the art. For example, in Step 7, 2-trimethylsilanylthiazole is treated with n-, sec-, or tert-butyl lithium, followed by lithium-zinc exchange with $ZnCl_2$. The organozinc reagent is coupled with the iodo pyrazolopyrimidine of formula (5) in the presence of a palladium catalyst, for example, dichloro[1,1'-bis(diphenyl-phosphino)ferrocene]palladium (II) dichloromethane, in an inert solvent, such as THF, at reflux temperature for about 12 to 36 hours, to provide a thiazole pyrazolopyrimidine of formula (6a).

Alternatively, in Step 8, a thiazole zinc bromide is generated using 5-bromo-4-methylthiazole and zinc metal, and used in the Negishi cross-coupling essentially as described for Step 7, to provide a thiazole pyrazolopyrimidine of formula (6b).

In Scheme 1, Step 9, a thiazole of formula (6a,b) is brominated to give a bromo or dibromo thiazole of formula (7), wherein $R^{3b}$=Br or $CH_3$. The thiazole is brominated with either 1 or 2 eq of N-bromosuccinimide, depending on whether $R^{ia}$ is $CH_3$ or H, respectively.

An alkyl thiazole of formula (8a-c) is obtained from either a thiazole of formula (6a,b) in Step 11, or from a bromothiazole of formula (7) in Step 10. In Step 10, halogen-lithium exchange with n-, sec-, or t-butyl lithium provides a thiazole lithium reagent, which is subsequently reacted with electrophiles, such as alkylhalides, like iodomethyl methylether or iodobutane. In Step 11, the thiazole lithium reagent is formed via deprotonation using n-, sec-, or tert-butyl lithium and then subsequently reacted with an electrophile, like iodomethyl methylether or iodobutane.

It will be appreciated by one skilled in the art that the thiazole ring system is readily functionalized and that thiazole intermediates such as 2-trimethylsilanyl-thiazole (Dondoni, A.; et. al. *J. Org. Chem.* 1988, 53, 1748) can be readily prepared. 5-Bromo-4-methylthiazole is obtained by bromination of 4-methylthiazole with bromine in acetic acid (Collins, I. J., et. al. WO2003093252, 13 Nov. 2003). 2,5-Dimethyl-4H-pyrazolo[1,5-a]pyrimidine-7-one (1) is readily prepared by condensation of ethyl acetoacetate and 5-methyl-2H-pyrazol-3-ylamine in refluxing acetic acid.

(II) dichloromethane or tetrakis(triphenylphosphine)palladium (0). The reaction is warmed to reflux temperature. Alternatively, the heterocyclic zinc reagent is formed from a haloheterocycle, such as 4-iodopyridine and zinc metal.

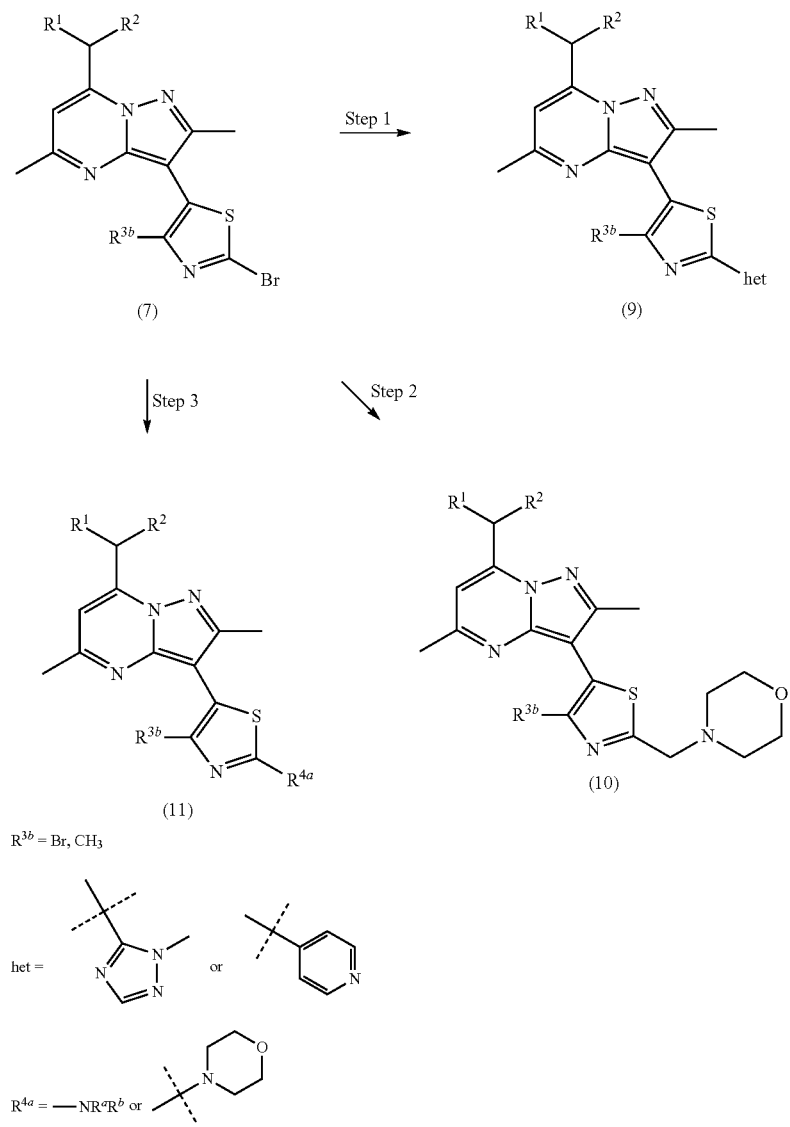

Scheme 2

Formation of a compound of formula (9), (10), or (11) can be carried out in accordance with reactions as depicted in Scheme 2. An appropriate compound of formula (9), (10), or (11) is one in which $R^1$, $R^2$, $R^a$, and $R^b$ are as defined for formula I and $R^{3b}$=Br or $CH_3$, and $R^{4a}$=—$NR^aR^b$ or —N-morpholinyl and "het" is defined as depicted.

In Step 1, a bromothiazole of formula (7) is coupled with a heterocyclic zinc reagent in a Negishi cross-coupling reaction to provide a thiazole heterocycle of formula (9). For example, 1-methyl-1,2,4-triazole is treated with n-, sec-, or tert-butyl lithium, followed by zinc chloride, at about −80 to −65° C., and reacted in situ with a bromothiazole of formula (7). The reaction is performed preferentially in an inert solvent, such as THF, in the presence of a palladium catalyst, such as dichloro[1,1'-bis(diphenyl - phosphino)ferrocene]palladium In Scheme 2, Step 2, an intermediate 2-formyl thiazole is formed via halogen-lithium exchange using n-, sec-, or t-butyl lithium followed by reaction with N-formyl morpholine. The formyl thiazole is subjected to a reductive amination in the presence of an organic amine, such as morpholine, to provide a morpholinyl methyl thiazole of formula (10). Reductive aminations are well-known in the art typically using an inorganic borohydride reagent such as sodium borohydride or sodium cyanoborohydride. Preferred conditions use sodium triacetoxyborohydride in an inert solvent such as dichloromethane or THF.

In Step 3, a bromothiazole of formula (7) undergoes a displacement reaction with an amine of formula —$NR^aR^b$ or with morpholine to provide an aminothiazole of formula (11). The reaction is preformed in an inert solvent, such as THF or dioxane, using an inorganic base, such as cesium carbonate at 70 to 110° C.

Scheme 3

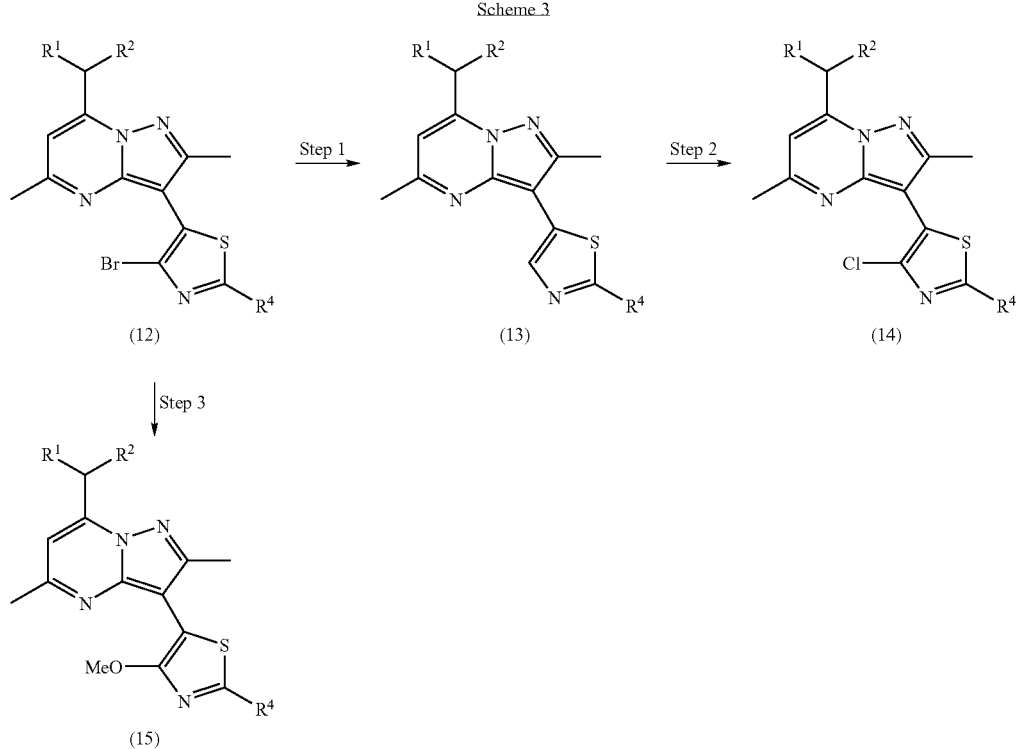

Formation of a compound of formula (13), (14), or (15) can be carried out in accordance with reactions as depicted in Scheme 3. An appropriate compound of formula (13), (14), or (15) is one in which R¹, R², and R⁴ are as defined for formula I.

It will be recognized by one skilled in the art that a 4-bromothiazole, such as that of formula (12) is readily manipulated to other functionality. For example, in Step 1, the bromide can be dehalogenated with cuprous chloride to give a thiazole of formula (13) which is subsequently chlorinated with N-chlorosuccinimide to provide a 4-chlorothiazole of formula (14).

In Scheme 3, Step 3, a 4-bromothiazole of formula (12) is displaced with sodium methoxide in the presence of copper (I) iodide in methanol at about 100 to 120° C. in an inert solvent such as dimethylformamide, to provide a 4-methoxy thiazole of formula (15).

Scheme 4

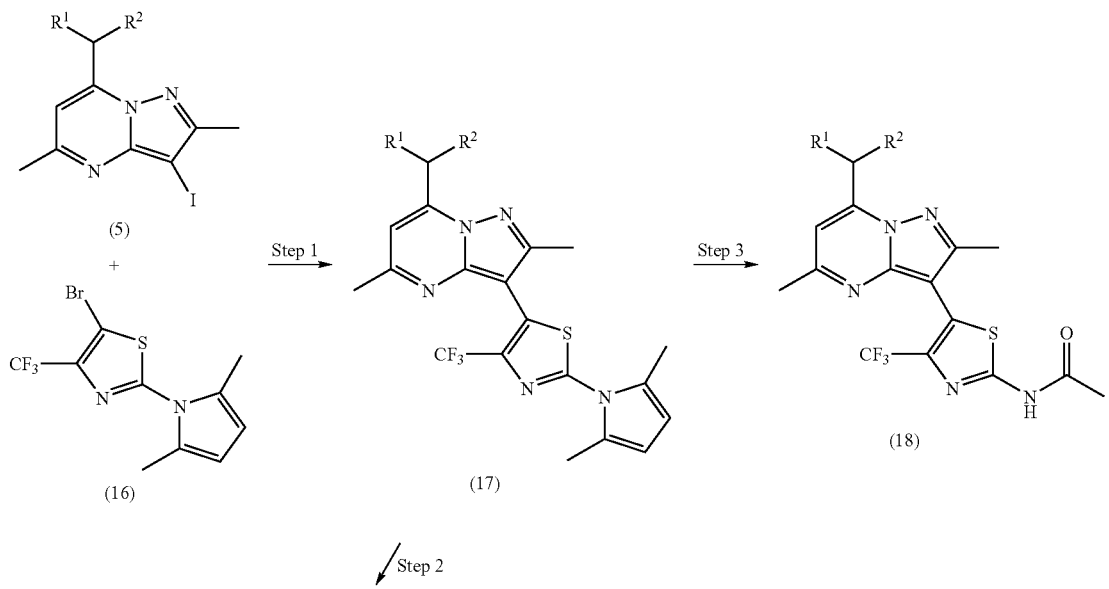

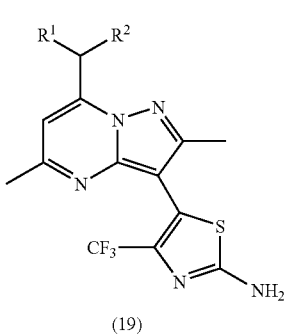 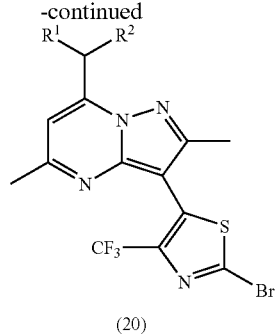 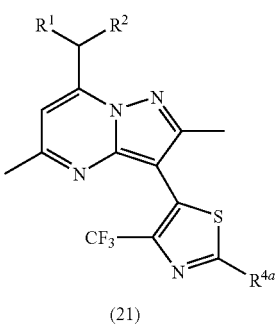

(19)     (20)     (21)

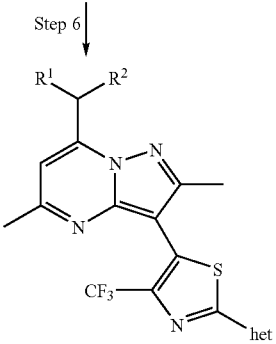

(20a)

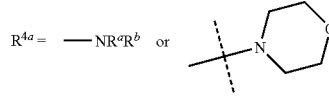

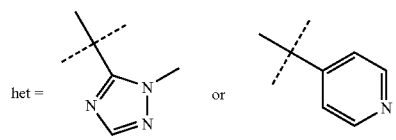

Formation of a compound of formula (17), (18), (19), (20), (20a), or (21) can be carried out in accordance with reactions as depicted in Scheme 4. An appropriate compound of formula (17), (18), (19), (20), (20a), or (21) is one in which $R^1$, $R^2$, $R^a$, and $R^b$ are as defined for formula I and $R^{4a}$ is —$NR^aR^b$ or —N-morpholinyl and "het" is defined as depicted.

In Scheme 4, Step 1, an iodopyrazolopyrimidine of formula (5) and a 5-bromothiazole of formula (16) undergo a Negishi cross-coupling to form a dimethylpyrrolylthiazole of formula (17). For example, the 5-bromothiazole of formula (16) is treated with n-, sec-, or tert-butyl lithium and then with zinc chloride at about −80 to −65° C. The organozinc reagent is reacted in situ with an iodopyrazolopyrimidine of formula (5). The coupling reaction is performed preferentially in an inert solvent, such as THF, at reflux temperature, in the presence of a palladium catalyst, such as bis(tri-t-butylphosphine) palladium (0).

In Step 2, a dimethylpyrrolylthiazole of formula (17) is deprotected to provide an aminothiazole of formula (19). The dimethylpyrrole is treated with hydroxylamine in acetic acid at a temperature of about 60 to 100° C., for about 4 to 8 h, preferably for about 6 h. In Step 3, to form the thiazole acetamide of formula (18), the same conditions are used as in Step 2, with the exception that the reaction is continued for about 72 h.

In Scheme 4, Step 4, a 2-aminothiazole of formula (19) is converted to a 2-bromothiazole of formula (20) using a modified Sandmeyer reaction. Preferred conditions use an alkylnitrite, such as t-butylnitrite, and copper (II) bromide, in acetonitrile at a temperature of about 60 to 80° C.

In Step 5, a 2-bromothiazole of formula (20) undergoes a displacement reaction with an amine of formula —$NR^aR^b$ or with morpholine to provide an aminothiazole of formula (21). The reaction is performed in an inert solvent, such as methanol, THF, or dioxane, or is treated neat, with an excess of the amine at a temperature of about 70 to 110° C. Alternatively the reaction is performed with the reacting amine and an excess of triethylamine, or an inorganic base, such as cesium carbonate. Also contemplated in the synthesis of aminothiazoles of formula (21) are various deprotection steps, such as removal of a tert-butyl ester carbamic acid (BOC), as may be required or beneficial for carrying out the reactions above wherein —$NR^aR^b$ carries additional amine functionality as defined for formula I. The selection and use of suitable protecting groups is well known and appreciated in the art (see for example, *Protecting Groups in Organic Synthesis*, Theodora Greene (Wiley-Interscience)).

In Scheme 4, Step 6, a 2-bromothiazole of formula (20) is coupled with a heterocyclic zinc reagent in a Negishi cross-coupling reaction to provide a thiazole heterocycle of formula (20a) in a manner similar to that as described for Scheme 2, Step 1.

It will be appreciated by the skilled artisan that a functionalized thiazole of formula (16) can be prepared by means known in the art. For example, cyclization of thiourea with a bromoketone, such as 3-bromo-1,1,1-trifluoropropan-2-one, provides 4-trifluoromethyl-thiazole-2-ylamine Subsequent bromination and protection of the amine using hexane-2,5-dione provides (16).

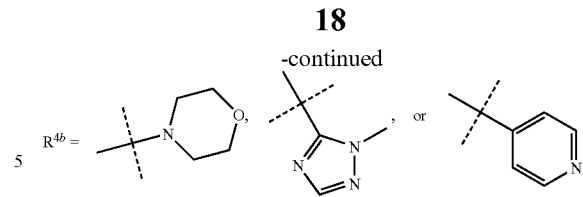

Formation of a compound of formula (23) can be carried out in accordance with reactions as depicted in Scheme 5. An appropriate compound of formula (23) is one in which $R^1$ and $R^2$ are as defined for formula I and $R^{4b}$ is defined as depicted.

An iodopyrazolopyrimidine of formula (5) and a 4-chloro-2-morpholino-thiazole, for example, of formula (22) undergo cross-coupling to form a pyrazolopyrimidine thiazole of formula (23). For example, the reactants are coupled in the presence of copper iodide, palladium acetate, and triphenylphosphine, with a base such as cesium carbonate. The coupling reaction is performed preferentially in an inert solvent, such as DMF, at about 100-150° C. for 4-24 h.

It will be appreciated by the skilled artisan that a functionalized thiazole of formula (22) can be prepared by means known in the art. For example, 2,4-dichlorothiazole can be reacted with morpholine to give the 2-morpholino-thiazole of formula (22). 2,4-Dichlorothiazole can also be exhaustively brominated to provide 2,5-dibromo-4-chlorothiazole. Subsequent bromine-lithium exchange with n-butyl lithium in THF at −90° C. and quench with water provides 2-bromo-4-chlorothiazole [*J. Chem. Soc. Perkin Trans I: Org Bioorg. Chem.* (1972-1999), (2):215-219 (1992)]. 2-Bromo-4-chlorothiazole can be subjected to a Negishi cross-coupling reaction with a heterocyclic zinc reagent to obtain the thiazol-2-yl triazole or pyridine.

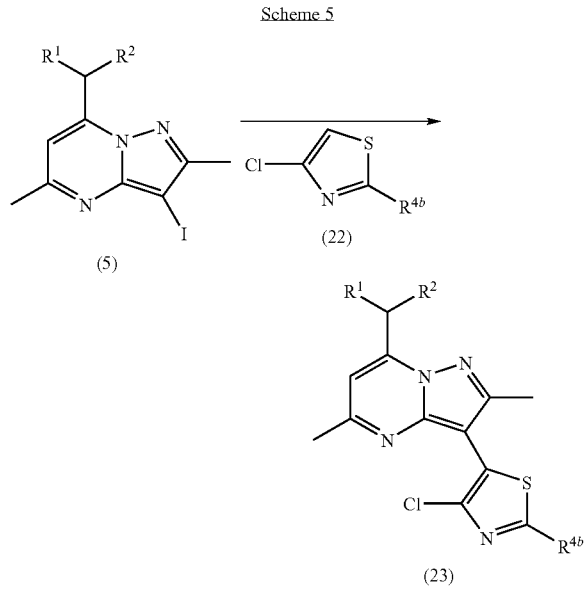

Scheme 5

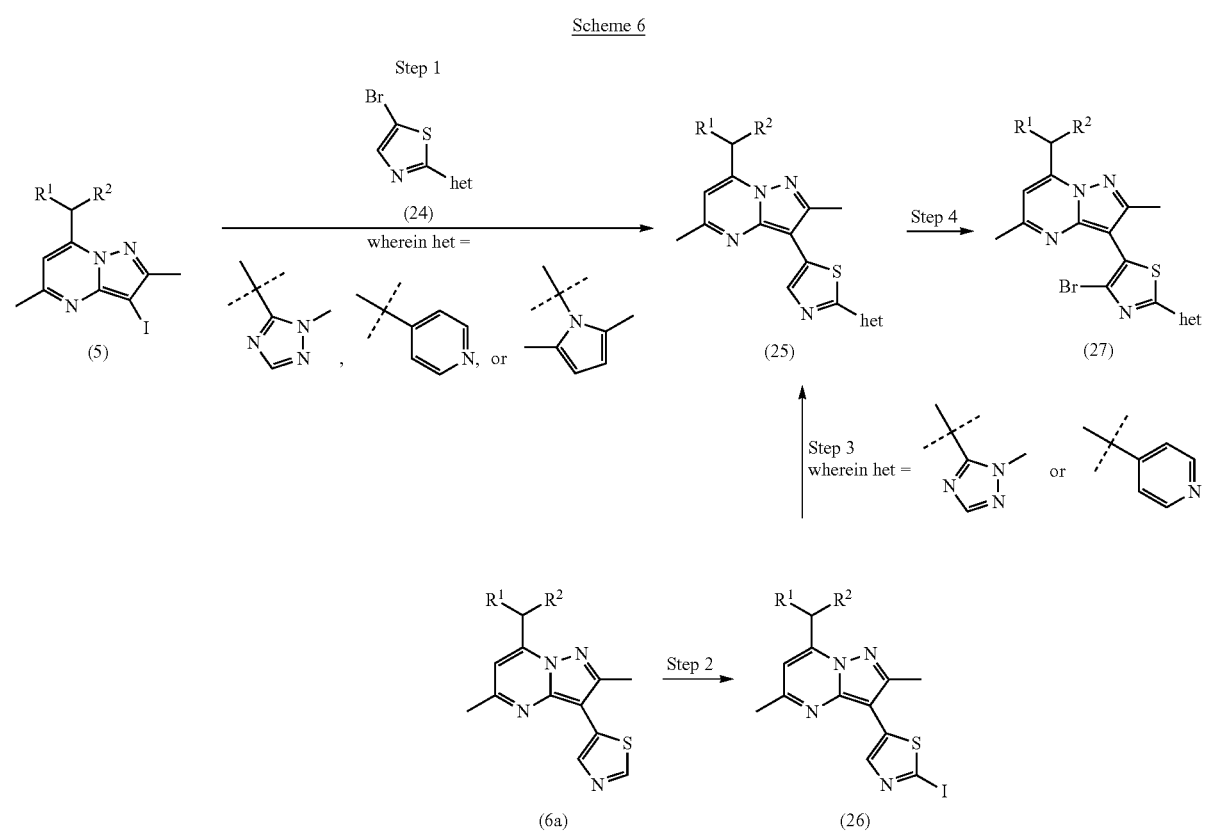

Scheme 6

Formation of a compound of formula (27) can be carried out in accordance with reactions as depicted in Scheme 6. An appropriate compound of formula (27) is one in which $R^1$ and $R^2$ are as defined for formula I and "het" is defined as depicted for Step 1 or Step 3, respectively.

In Scheme 6, Step 1, a heterocyclic thiazole, for example, of formula (25) is obtained by reaction of an iodopyrazolopyrimidine of formula (5) with a bromothiazole of formula (24). The reaction is performed in the presence of N-butylammonium bromide and a base, such as potassium acetate with a palladium catalyst such as palladium acetate with tris(2,4-di-tert-butyl-phenyl)-phosphane, in an inert solvent such as N-methylpyrrolidinone at a temperature of about 100-150° C.

Alternatively, in Step 2, a thiazolyl pyrazolopyrimidine of formula (6a) is iodinated to provide a 2-iodothiazole of formula (26). The thiazole is treated with lithium diisopropylamide at a temperature of −70 to −80° C. for about one hour and then treated with N-iodosuccinimide at about the same temperature in an inert solvent, such as THF. This is followed by Step 3, wherein a triazolyl or 4-pyridyl thiazole of formula (25) is formed using Negishi cross-coupling conditions similar to those described for Scheme 2, Step 1.

In Scheme 6, Step 4, a thiazolyl pyrazolopyrimidine of formula (25) is brominated to give a bromothiazole of formula (27). The bromination is effected using N-bromosuccinimide in the presence of a small amount of acetic acid in an inert solvent, such as acetonitrile.

A compound of formula (27), wherein het=2,5-dimethyl-pyrrol-1-yl, can be further elaborated to obtain compounds of the invention as described in Scheme 4, Steps 2, 3, 4, and 5.

It will be appreciated by the skilled artisan that heterocycle thiazoles of formula (24) can be readily prepared by means known in the art. For example, thiazole-2-carboxylic acid amide can be cyclized to the triazole with 1,1-dimethoxy-N,N-dimethyl-methanamine, followed by N-methyl-hydrazine to obtain the triazolyl thiazole, which can be subsequently brominated with N-bromosuccinimide. Literature procedures afford 4-thiazol-2-yl-pyridine which can be brominated to provide 4-(5-bromo-thiazol-2-yl)-pyridine. 5-Bromo-2-(2,5-dimethyl-pyrrol-1-yl)-thiazole can be readily obtained by reaction of 2-amino-5-bromothiazole with hexane-2,5-dione.

As used herein, "TLC" refers to thin layer chromatography; "HPLC" refers to high performance liquid chromatography; "LC/MS" refers to liquid chromatography/mass spectrometry; "GC/MS" refers to gas chromatography/mass spectrometry"; "HR-ToF" refers to high resolution time-of-flight; "APCI" refers to atmospheric pressure chemical ionization; "δ" refers to part per million down-field from tetramethylsilane; "THF" refers to tetrahydrofuran; "EtOAc" refers to ethyl acetate; "MeOH" refers to methanol; "EtOH" refers to ethanol; "DMF" refers to dimethylformamide.

EXAMPLES

Without further elaboration, it is believed that one skilled in the art can, using the preceding description, practice the present invention to its fullest extent. The following preparations and examples are provided to describe the invention in further detail. They are intended to illustrate and not to limit the invention in any way whatsoever. The reagents and starting materials are readily available to, or may be readily synthesized by, one of ordinary skill in the art. Examples 1-35 provide representative compounds and illustrate the preparation thereof Examples A-D illustrates various biological assays that can be used for determining the biological properties of the compounds of the inventions. Those skilled in the art will promptly recognize appropriate variations from the procedures described in the examples. The names of the compounds of the present invention are provided by ChemDraw Ultra® version 7.0.1. Salts are named as the free base plus the conjugate acid.

Preparation 1

2,5-Dimethyl-4H-pyrazolo[1,5-a]pyrimidin-7-one

Add ethyl acetoacetate (128 g, 0.98 mol) dropwise to an acetic acid solution (500 mL) of 5-methyl-2H-pyrazol-3-ylamine (100 g, 0.95 mol), keeping the temperature at 25-28° C. Heat the mixture at reflux for 10 h and then cool to room temperature. Add the reaction to tert-butyl methyl ether (5 L) cooled to 5° C., keeping the temperature below 10° C. Stir for 1 h at 5° C., and filter. Dry the resulting material in vacuo overnight to provide a white solid (158 g, 96%).

Preparation 2

7-Chloro-2,5-dimethyl-pyrazolo[1,5-a]pyrimidine

To a suspension of 2,5-dimethyl-4H-pyrazolo[1,5-a]pyrimidin-7-one (10.0 g, 61.3 mmol) in toluene (150 mL) add N,N-dimethylaniline (9.7 mL, 76.7 mmol). Add phosphorus oxychloride (11.2 mL, 122.6 mmol) dropwise to this white suspension. Reflux for 3 h under an inert atmosphere, cool to room temperature, and concentrate the reaction to a brown oil using reduced pressure. Dissolve the oil in ethyl acetate (250 mL) and basify with 1.0 N NaOH. Separate the organic phase and extract the basic aqueous phase with ethyl acetate (2×100 mL). Combine the organic phases, dry over anhydrous magnesium sulfate, filter, and concentrate under reduced pressure to yield a brown solid. Purify the material using flash chromatography, eluting with 80% hexane/20% (30% THF/hexane) to 0% hexane/100% (30% THF/hexane) in a step gradient of 20% increments to provide a light green solid (6.65 g, 59%). ES/MS m/z ($^{35}$Cl) 182.3 (M+1)⁻.

Alternate Procedure:

Add 2,5-dimethylpyrazolo[1,5-a]pyrimidin-7-one (20 g, 122 mmol) to 1,4-dioxane (60 mL). Stir the mixture at 22° C. for 10 min and then add N,N-diethylaniline (20.8 mL, 128 mmol). Stir for an additional 5 min and then add phosphorus oxychloride (11.7 mL, 126 mmol) over 15 min. Stir the mixture at 22° C. for 15 min, then heat to 80-85° C. over 35 min and hold the reaction at this temperature for 1.5 h. Add the cooled reaction mixture slowly to a solution of potassium phosphate dibasic (106.7 g, 612.82 mmol) in water (325 mL) cooled to 0-5° C., keeping the temperature below 5° C. during the addition. Stir the mixture at 22° C. and then add methyl-t-butyl ether (150 mL). Separate the organic layer and extract the aqueous layer with methyl-t-butyl ether (2×100 mL). Combine the organic portions, dry over sodium sulfate, filter, and evaporate the solvent. Purify by silica gel chromatography, eluting with hexanes/ethyl acetate (2/1) to provide the title compound as a yellow solid (20.7 g, 88%). ES/MS m/z ($^{35}$Cl) 182 (M+1)$^+$.

Preparation 3

7-(1-Propyl-butyl)-2,5-dimethyl-pyrazolo[1,5-a]pyrimidine

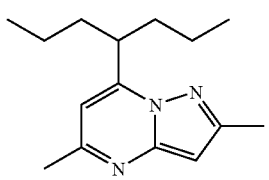

Charge an oven dried flask equipped with a reflux condenser, with anhydrous THF (40 mL), iodine (catalytic amount), magnesium ribbon (1.92 g, 78 9 mmol) and 4-bromoheptane (9.4 mL, 52 mmol). Heat the reaction to reflux in an oil bath. The temperature of the reaction spikes as the Grignard reaction is initiated. Stir the reaction an additional 4 h at 90° C. and cool to room temperature. Allow the magnesium metal to settle out (can also be centrifuged) and canulate off the Grignard reagent under positive argon pressure into a flask charged with 7-chloro-2,5-dimethylpyrazolo [1,5-a]pyrimidine (4.80 g, 26.3 mmol) in anhydrous toluene (20 mL). Reflux the reaction under an inert atmosphere overnight. Cool the reaction to room temperature and quench with water. Dilute with ethyl acetate (150 mL), then add water (100 mL) and saturated ammonium chloride (50 mL). Separate and extract the aqueous phase with dichloromethane (75 mL). Combine the organic phases, dry over anhydrous magnesium sulfate, filter, and concentrate under reduced pressure. Purify the resulting residue using flash chromatography, eluting with 80% hexane/20% (20% ethyl acetate/hexane) to 0% hexane/100% (20% ethyl acetate/hexane) in a step gradient of 20% increments to give yellow crystals (3.08 g, 48%). ES/MS m/z 246.3 (M+1)$^+$.

Alternate Procedure:

Heat a mixture of magnesium turnings (3.5 g, 144 mmol) and a catalytic amount of iodine (100 mg) in THF (100 mL) to 65° C. under a nitrogen atmosphere. Add a few drops of neat 4-bromoheptane and heat the mixture until the reaction starts. Then add a solution of 4-bromoheptane (17.6 mL, 94 9 mmol) in THF (42 mL) keeping the temperature at 65-70° C. over 2 h. Reflux the mixture for an additional hour and then cool the reaction to 22° C. Add the prepared Grignard reagent to a solution of 7-chloro-2,5-dimethyl-pyrazolo[1,5-a]pyrimidine (10.2 g; 53 3 mmol) in THF (60 mL) cooled to 0° C. under a nitrogen atmosphere. Add the magnesium reagent solution via cannula over 45 min while keeping the temperature below 10° C. Then stir the mixture for an additional 30 min at 5° C. Add to this mixture a 10% aqueous ammonium chloride solution (wt/wt) (125 mL) and stir at 22° C. for 30 min. Separate the organic layer and extract the aqueous layer with ethyl acetate (2×25 mL). Combine the organic layers and dry over sodium sulfate. Filter the mixture and evaporate the solvent. Purify the crude material by silica gel flash chromatography using an eluent of hexanes/ethyl acetate (5/1) to provide the title compound (8 g, 62%). ES/MS m/z 246 (M+1)$^+$.

Preparation 3a 7-(1-Propyl-butyl)-2,5-dimethyl-pyrazolo[1,5-a]pyrimidine

Alternate Route

Step 1: 3-Acetyl-3-oxo-4-propyl-heptanoic acid ethyl ester

Add magnesium chloride (14.63 g, 153.70 mmol) to dichloromethane (500 mL) followed by addition of ethyl acetoacetate (19.55 mL, 20.00 g, 153.79 mmol) all at once and stir at room temperature for one hour. Cool the mixture in an ice water bath and and add pyridine (24.86 mL, 24.32 g, 307.39 mmol) dropwise. Add di-n-propylacetyl chloride (25.00 g, 153.70 mmoles) dropwise at 0° C. under nitrogen to the white slurry. After the addition is complete remove the cooling bath, warm to ambient temperature, and stir for 16 h. Quench the reaction with 1 N HCl (400 mL) and separate the bottom layer. Dry the organic portion over magnesium sulfate, filter, and concentrate under vacuum to give a yellow oil (34 g, 86%). Use the material directly in the next step without further purification.

Step 2: 5-Propyl-octane-2,4-dione

Dissolve 3-acetyl-3-oxo-4-propyl-heptanoic acid ethyl ester (32.4 g, 126.39 mmoles) in dimethyl sulfoxide (100 mL) and water (5 mL). Heat the solution at 150° C. for 6 to 8 h or follow the reaction by GC/MS. Cool the reaction and extract with heptane (3×100 mL). Wash the combined organic portions with water (100 mL) and brine (100 mL). Concentrate under vacuum at 50° C. to remove most of the heptane. Obtain 23.29 g of an oil and use directly in the next step.

Step 3: 7-(1-Propyl-butyl)-2,5-dimethyl-pyrazolo[1,5-a]pyrimidine

Mix 5-propyl-octane-2,4-dione (15 g, 81.40 mmoles) in acetic acid (15 mL) and cool in an ice bath. Add 5-amino-3-methylpyrazole (7.91 g, 81.40 mmol) portionwise and stir at ambient temperature. Check for completion of the reaction by GC/MS after 3 h. GC indicates correct region isomer in comparison with an authentic sample. Distill off the excess acetic acid. Add water (50 mL) and extract with heptane (50 mL). Wash the heptane with brine (50 mL). Dry the organic layer over MgSO$_4$, filter, and concentrate under vacuum to give a crude oil (15.8 g, 79%). $^1$H NMR (CDCl$_3$): 6.39 (s, 1H); 6.31 (s, 1H); 3.75 (m, 1H); 2.55 (s, 3H); 2.45 (s, 3H); 1.71 (q, 4H); 1.23 (m, 4H); 0.85 (t, 6H).

Prepare the following compound essentially as described in Preparation 3, using either procedure. Use 3-bromopentane to prepare the Grignard reagent.

| Prep. No. | Chemical name | Physical data |
| --- | --- | --- |
| 4 | 7-(1-Ethyl-propyl)-2,5-dimethyl-pyrazolo[1,5-a]pyrimidine | ES/MS m/z 218.1 (M + 1)$^+$ |

Preparation 5

7-(1-Propyl-butyl)-3-iodo-2,5-dimethyl-pyrazolo[1,5-a]pyrimidine

Dissolve 7-(1-propyl-butyl)-2,5-dimethyl-pyrazolo[1,5-a]pyrimidine (3.08 g, 12.5 mmol) in anhydrous acetonitrile (25 mL) and add 6 portions (0.70 g each) of N-iodosuccinimide (4.2 g, 18.7 mmol) at 10 minute intervals. Stir over the weekend at room temperature. Strip off the acetonitrile and dilute the oil with dichloromethane (100 mL). Wash with saturated ammonium chloride solution (2×50 mL). Collect the organic phase, dry over anhydrous magnesium sulfate, filter, and concentrate under reduced pressure to yield a dark red oil. Purify the oil using flash chromatography, eluting with 100% hexane/0% (20% ethyl acetate/hexane) to 0% hexane/100% (20% ethyl acetate/hexane) in a step gradient of 50% increments to give an orange oil (10.97 g, 87%).

$^1$H NMR (400 MHz, CDCl$_3$): 6.42 (s, 1H), 3.74-3.70 (m, 1H), 2.58 (s, 3H), 2.46 (s, 3H), 1.74-1.68 (m, 4H), 1.28-1.14 (m, 4H), 0.84 (t, J=7.0 Hz, 6H).

Prepare the compound below essentially as described in Preparation 5.

| Prep. No. | Chemical name | Physical data |
|---|---|---|
| 6 | 7-(1-Ethyl-propyl)-3-iodo-2,5-dimethyl-pyrazolo[1,5-a]pyrimidine | 1H NMR (400 MHz, CDCl$_3$): 6.44 (s, 1H), 3.59 (m, 1H), 2.61 (s, 3H), 2.49 (s, 3H), 1.86-1.76 (m, 4H), 0.85 (t, J = 7.5 Hz, 6H). |

Alternate Procedure for Preparation 6:

Add acetic acid (1 mL) and N-iodosuccinimide (6.7 g, 29 9 mmol) in one portion to a solution of 7-(1-ethyl-propyl)-2,5-dimethyl-pyrazolo[1,5-a]pyrimidine (6 g, 27.5 mmol) in acetonitrile (60 mL). Stir the mixture at 22° C. for 2 h. Evaporate the solvent and take the residue up in water (50 mL) and methyl-t-butyl ether (100 mL). Separate the organic portions, dry over sodium sulfate, filter, and evaporate the solvent to afford the title compound (9.2 g, 96%). ES/MS m/z 344 (M+1)$^+$.

Preparation 7

2-Trimethylsilanyl-thiazole

Mix n-butyl lithium (20.4 mL, 51.0 mmol, 2.5 M in hexane) with diethyl ether (50 mL) in a three-necked flask, equipped with a dropping funnel and thermometer. Cool to −78° C. and add dropwise a solution of thiazole (4.25 g, 50.0 mmol) in diethyl ether (50 mL). After the addition is complete, stir the reaction mixture at −78° C. for 30 min, followed by addition of chlorotrimethylsilane (5.4 g, 50.0 mmol). Stir at −78° C. for an hour and then warm to room temperature. Quench the reaction by adding saturated sodium bicarbonate. Extract the aqueous layer with diethyl ether. Wash the combined organic portions with brine and dry over sodium sulfate. Filter and concentrate under reduced pressure to give a residue. Purify by distillation to give 8.33 g (52-56° C./15 mm Hg) of title compound. $^1$H NMR (400 MHz, CDCl$_3$) 8.13 (d, 1H, J=2.6 Hz), 7.54 (d, 1H, J=2.6 Hz), 0.43 (s, 9H).

Preparation 8

5-Bromo-4-methylthiazole

Add bromine (9.27 mL, 182 mmol) to a solution of 4-methylthiazole (15.0 g, 152 mmol) in acetic acid (30 mL) at 0° C. Slowly warm the reaction mixture to room temperature and stir overnight. Dilute with dichloromethane and wash with 1 N NaOH and brine. Dry the organic layer over sodium sulfate, filter, and concentrate under vacuum. Purify the crude product by silica gel column chromatography, elueting with hexanes/ethyl acetate (5/1) to obtain the title compound (9.94 g, 37%). $^1$H NMR (400 MHz, CDCl$_3$): δ 8.69 (s, 1H), 2.43 (s, 3H).

Preparation 9

Thiazole-2-carboxylic acid ethyl ester

To a mixture of 2-trimethylsilylthiazole (135 g, 858 1 mmol) in toluene (1350 mL) add a solution of ethyl chloroformate (98.4 mL, 1.03 mol) in toluene (1350 mL) over 15 min. Stir the reaction at 22° C. for 2 h. Add the solution over aqueous sodium carbonate 25% (wt/wt) (5 L) and stir for 30 min. Separate the organic layer and re-extract the aqueous layer with methylene chloride (2×1 L). Combine the organic layers and evaporate the solvent to provide the title compound (134 g, 99%). ES/MS m/z 158 (M+1)$^+$.

Preparation 10

Thiazole-2-carboxylic acid amide

Add thiazole-2-carboxylic acid ethyl ester (150 g, 0.9 mol) to a mixture of methanol (75 mL) and 30% aqueous ammonium hydroxide (750 mL) and heat the mixture at reflux for 1 h. Then cool to 22° C. and evaporate the methanol under vacuum. Stir the mixture for 30 min at room temperature and filter the solid. Dry the isolated solid under vacuum to afford the title compound (98 g, 85%). ES/MS m/z 129 (M+1)$^+$.

Preparation 11

1-Methyl-5-thiazol-2-yl-1H-[1,2,4]triazole

Cool 1,1-dimethoxy-N,N-dimethyl-methanamine (240 mL) to 10° C. and add thiazole-2-carboxylic acid amide (60 g, 421 mmol) in three portions. Stir the mixture at 10° C. for 30 min. Then heat the mixture gradually to reflux in 45 min. Distill off the methanol formed and then heat the reaction to 100° C. for 1.5 h. Cool the mixture to 60° C. and remove the excess 1,1-dimethoxy-N,N-dimethyl-methanamine by vacuum distillation. Cool the residue to 22° C. and add hexanes (200 mL). Triturate the mixture for 15 min, filter, and dry the solid to constant weight before using in the next step.

Add the solid isolated above (68 g) to acetic acid (680 mL) and cool the mixture to 10° C. Add N-methyl-hydrazine (27 mL, 509 mmol) at such a rate as to keep the temperature below 15° C. Warm the mixture to 20° C. in 30 min and then heat gradually to 90° C. Stir at 90° C. for 30 min and then cool to 22° C. Remove the acetic acid by vacuum distillation. Add the residue over water and adjust to pH=8 by adding 25% aqueous sodium hydroxide solution. Extract the aqueous layer with methyl-t-butyl ether (3×600 mL). Combine the organic layers and evaporate the solvent. Purify the resulting residue by silica gel chromatography using an eluent of hexanes/isopropanol (9/1) to provide the title compound (49 g, 70%). ES/MS m/z 167 (M+1)$^+$.

Preparation 12

5-(5-Bromo-thiazol-2-yl)-1-methyl-1H-[1,2,4]triazole

To a mixture of methyl-5-thiazol-2-yl-1H-[1,2,4]triazole (6.55 g; 39 4 mmol) and dimethylformamide (32 mL), add N-bromosuccinimide (14 g, 78.8 mmol) in three portions over 1 h. Stir the mixture at 22° C. for 18 h and then add to water (300 mL) chilled to 0-5° C. Separate the aqueous layer and extract with methyl-t-butyl ether (2×200 mL). Combine the organic layers and wash with 7% aqueous sodium hydrogen carbonate (100 mL) and then dry over sodium sulfate. Filter and evaporate the solvent to afford the title compound (9.5 g, 93%). ES/MS m/z ($^{79}$Br/$^{81}$Br) 245/247 (M+1)$^+$.

Preparation 13

2,5-Dimethyl-3-[2-(2-methyl-2H-[1,2,4]triazol-3-yl)-thiazol-5-yl]-7-(1-propyl-butyl)-pyrazolo[1,5-a]pyrimidine Combine 5-(5-bromo-thiazol-2-yl)-1-methyl-1H-[1,2,4]triazole (6.5 g, 23 8 mmol) and 2,5-dimethyl-7-(1-propyl-butyl)-pyrazolo[1,5-a]pyrimidine (6 g, 24 5 mmol) in N-methylpyrrolidinone (58 mL) and stir to complete solution under nitrogen. Then add tetra-N-butylammonium bromide (5.47 g, 16.7 mmol) and potassium acetate (11.8 g, 119 mmol) and heat the mixture to 100° C. under a nitrogen atmosphere. Degas the hot mixture by three cycles of vacuum/nitrogen purge. Then add palladium acetate (216 mg, 0.94 mmol) and tris(2,4-di-tert-butyl-phenyl)-phosphane (787 mg, 1.2 mmol). Heat the mixture 4 h at 125° C. under nitrogen. Cool the mixture to 22° C. and add to water (750 mL). Extract the aqueous layer with methyl-t-butyl ether (3×200 mL), combine the organic portions, and evaporate. Purify the residue by filtration through a silica gel pad eluting with hexanes/ethyl acetate (4/1). Combine the product containing fractions and evaporate the solvent to afford the title compound (7 g, 72%). ES/MS m/z 410 (M+1)$^+$.

Preparation 14

2,5-Dimethyl-7-(1-propyl-butyl)-3-thiazol-5-yl-pyrazolo[1,5-a]pyrimidine

Charge an oven dried flask with 2-trimethylsilanylthiazole (1.765 g, 11.24 mmol) dissolved in anhydrous THF (30 mL) and chill under an inert atmosphere to –78° C. Slowly add n-butyl lithium (2.5 M hexane solution, 4.5 mL, 11.24 mmol) and stir 30 min at –78° C. Add anhydrous zinc chloride (2.26 g, 16.58 mmol) in one aliquot and stir 30 min at –78° C. Allow the reaction to rise to room temperature, stir 30 min, and add 7-(1-propyl-butyl)-3-iodo-2,5-dimethyl-pyrazolo[1,5-a]pyrimidine (1.624 g, 5.18 mmol) and dichloro[1,1'-bis(diphenylphosphino)ferrocene]palladium (II) dichloromethane (0.423 g, 0.518 mmol). Reflux overnight in an oil bath (90° C.) under an inert atmosphere. Cool the reaction to room temperature, quench with saturated sodium bicarbonate, and dilute with ethyl acetate (150 mL). Separate and extract the aqueous with ethyl acetate (75 mL). Combine the organic phases, dry over anhydrous magnesium sulfate, filter, and concentrate under reduced pressure. Purify the resulting residue using flash chromatography, eluting with 100% hexane/0% (30% THF/hexane) to 0% hexane/100% (30% THF/hexane) in a step gradient of 10% increments to give a white solid (0.720 g, 42%). ES/MS m/z 329.0 (M+1)$^+$.

Prepare the compound below essentially as described in Preparation 14.

| Prep. No. | Chemical name | Physical data |
|---|---|---|
| 15 | 7-(1-Ethyl-propyl)-2,5-dimethyl-3-thiazol-5-yl-pyrazolo[1,5-a]pyrimidine | 1H NMR (400 MHz, CDCl$_3$): d 8.75 (s, 1H), 8.75 (s, 1H), 8.28 (s, 1H), 6.47 (s, 1H), 3.62-3.55 (m, 1H), 2.65 (s, 3H), 2.61 (s, 3H), 1.89-1.75 (m, 4H), 0.85 (t, 6H, J = 7.5 Hz), 0.85 (t, 6H, J = 7.5 Hz). |

Alternate Procedure for Preparation 15:

Add n-butyl lithium (76.5 mL, 191 mmol, 2.5 M in hexanes) to a solution of 2-trimethylsilylthiazole (30 g, 191 mmol) in THF (450 mL) at –78° C. under nitrogen, keeping the temperature below –74° C. during the addition. Stir the mixture at –78° C. for 30 min and then add zinc chloride, dry powder, (39.9 g, 286 mmol) in one portion and warm the mixture to 22° C. over one hour. Add 7-(1-ethyl-propyl)-3-iodo-2,5-dimethyl-pyrazolo[1,5-a]pyrimidine, (30 g, 87 mmol) and 1,1'-bis(diphenylphosphino)ferrocene palladium (II) chloride (6.5 g, 8 mmol) and heat the mixture to reflux under nitrogen for 8 h. Cool the mixture to 22° C. and add 10% aqueous ammonium chloride (450 mL). Separate the organic layer and wash the aqueous layer with methyl-t-butyl ether (2×100 mL). Combine the organic portions, dry over sodium sulfate, filter, and evaporate the solvent to afford the title compound (20.4 g, 78%). ES/MS m/z 301 (M+1)$^+$.

Preparation 16

7-(1-Ethyl-propyl)-3-(2-iodo-thiazol-5-yl)-2,5-dimethyl-pyrazolo[1,5-a]pyrimidine Add a freshly prepared solution of lithium di-i-propylamide (150 ml; 62 4 mmol, 0.6 M in THF) to a mixture of 7-(1-ethyl-propyl)-2,5-dimethyl-3-thiazol-5-yl-pyrazolo[1,5-a]pyrimidine, (17.8 g, 62 4 mmol) in THF (100 mL) at –78° C. under a nitrogen atmosphere, keeping the temperature below –74° C. during the addition. Stir the mixture at –78° C. for one hour and then add a solution of N-iodosuccinimide (15 g, 63 mmol) in THF (100 mL) keeping temperature below –74° C. Warm the reaction gradually to 22° C. and then add a 10% aqueous solution of ammonium chloride (300 mL). Separate the organic layer and wash the aqueous layer with methyl-t-butyl ether (2×200 mL). Combine the organic layers, dry over sodium sulfate, filter, and evaporate the solvent. Purify the resulting residue by silica gel chromatography, eluting with hexanes/acetone (5/1) to afford the title compound (15 g, 60%). ES/MS m/z 427 (M+1)$^+$.

Example 1

7-(1-Ethyl-propyl)-2,5-dimethyl-3-(4-methyl-thiazol-5-yl)-pyrazolo[1,5-a]pyrimidine Add Rieke® zinc (10 g in 100 mL of THF, 13.2 mL, 18.48 mmol) to 5-bromo-4-methylthiazole (2.13 g, 18.48 mmol) and heat at reflux for 2 h. Cool the mixture to room temperature and settle the zinc down by centrifuge. Bubble nitrogen gas through 7-(1-ethyl-propyl)-3-iodo-2,5-dimethyl-pyrazolo[1,5-a]pyrimidine (900 mg, 2.62 mmol) in dry tetrahydrofuran (10 mL) and add the organozinc bromide solution followed by addition of [1,1'-bis(diphenylphosphino)ferrocene]-dichloropalladium(II) (106 mg, 0.13 mmol). Stir the reaction mixture under reflux overnight and cool to room temperature. Add ammonium chloride solution to the reaction mixture and extract with dichloromethane. Dry the organic portion over sodium sulfate, filter, and remove the solvent under vacuum. Purify the crude product by silica gel column chromatography, elueting with hexane/ethyl acetate (3/1) to obtain the title compound (652 mg, 79%). $^1$H NMR (400 MHz, CDCl$_3$): δ 8.80 (s, 1H), 6.48 (s, 1H), 3.63 (m, 1H), 2.57 (s, 3H), 2.43 (s, 3H), 2.40 (s, 3H), 1.85 (m, 4H), 0.90 (t, 6H, J=7.3Hz). ES/MS m/z 315 (M+1)$^+$.

Preparation 17

3-(2,4-dibromo-thiazol-5-yl)-2,5-dimethyl-7-(1-propyl-butyl)-pyrazolo[1,5-a]pyrimidine Dissolve 2,5-dimethyl-7-(1-propyl-butyl)-3-thiazol-5-yl-pyrazolo[1,5-a]pyrimidine (3.15 g, 9.59 mmol) in acetonitrile (100 mL) and add N-bromosuccinimide (4.27 g, 24.0 mmol) in one aliquot. Stir overnight under an inert atmosphere and confirm the reaction is complete using TLC. Concentrate under reduced pressure, dilute the oil with dichloromethane (150 mL), and wash with water (75 mL). Dry the organic phase over anhydrous magnesium sulfate, filter, and concentrate under reduced pressure. Purify the resulting oil using flash chromatography, eluting with 100% hexane/0% (30% THF/hexane) to 0% hexane/100% (30% THF/hexane) in a step gradient (0-10-15-20-25-30-35-40-45-50-100% of 30% THF/hexane) to give yellow crystals (3.70 g, 79%). ES/MS m/z ($^{79}$Br$^{81}$Br) 486.7 (M+1)$^+$.

Prepare the compounds below essentially as described in Preparation 17, with the exception that dichloromethane is used as the solvent.

| Ex. No. | Chemical name | Physical data |
|---|---|---|
| 2 | 3-(2,4-Dibromo-thiazol-5-yl)-7-(1-ethyl-propyl)-2,5-dimethyl-pyrazolo[1,5-a]pyrimidine | MS (APCI) m/z ($^{79}$Br$^{81}$Br) 459.1 (M + 1)$^+$ |
| 3* | 3-(2-Bromo-4-methyl-thiazol-5-yl)-7-(1-ethyl-propyl)-2,5-dimethyl-pyrazolo[1,5-a]pyrimidine | ES/MS m/z ($^{79}$Br) 393 (M + 1)$^+$ |

*Use 1.1 eq NBS and stir for 3 days.

Example 4

3-(4-Bromo-2-morpholin-4-yl-thiazol-5-yl)-2,5-dimethyl-7-(1-propyl-butyl)-pyrazolo[1,5-a]pyrimidine

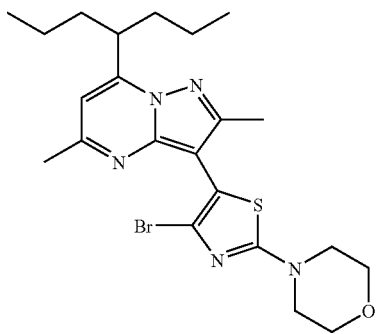

Charge an oven dried flask with 3-(2,4-dibromothiazol-5-yl)-2,5-dimethyl-7-(1-propyl-butyl)-pyrazolo[1,5-a]pyrimidine (0.973 g, 2.00 mmol), anhydrous dioxane (20 mL), morpholine (0.872 g, 10.0 mmol), and cesium carbonate (1.95 g, 6.00 mmol). Reflux in an oil bath (105° C.) under an inert atmosphere overnight. Confirm the reaction is complete using LC/MS. Dilute with ethyl acetate (100 mL), wash with water (50 mL), and back extract the aqueous with ethyl acetate (50 mL). Combine the organic phases, dry over magnesium sulfate, filter, and concentrate under reduced pressure. Purify the resulting residue using flash chromatography, eluting with 100% hexane/0% (40% dichloromethane/20% ethyl acetate/2% 7 N ammonia in methanol/38% hexane) to 0% hexane/100% (40% dichloromethane/20% ethyl acetate/2% 7 N ammonia in methanol/38% hexane) in a step gradient of 10% increments to yield an off-white solid (0.878 g, 89%). ES/MS m/z ($^{79}$Br) 491.7 (M+1)$^+$.

Prepare the following examples essentially as described in Example 4, using as the amine either 2.0 dimethylamine/THF or morpholine, and using THF or dioxane as the solvent. Run reactions in a sealed vessel or Schlenk tube.

| Ex. No. | Chemical name | Physical data |
|---|---|---|
| 5* | {4-Bromo-5-[2,5-dimethyl-7-(1-propyl-butyl)-pyrazolo[1,5-a]pyrimidin-3-yl]-thiazol-2-yl}-dimethylamine | ES/MS ($^{79}$Br) 449.8 (M + 1)$^+$. |
| 6 | 3-(4-Bromo-2-morpholin-4-yl-thiazol-5-yl)-7-(1-ethyl-propyl)-2,5-dimethyl-pyrazolo[1,5-a]pyrimidine | MS (APCI) m/z ($^{81}$Br) 466.5 (M + 1)$^+$ |
| 7 | {4-Bromo-5-[7-(1-ethyl-propyl)-2,5-dimethyl-pyrazolo[1,5-a]pyrimidin-3-yl]-thiazol-2-yl}-dimethyl-amine | MS (APCI) m/z ($^{81}$Br) 424.4 (M + 1)$^+$ |
| 8 | {5-[7-(1-Ethyl-propyl)-2,5-dimethyl-pyrazolo[1,5-a]pyrimidin-3-yl]-4-methyl-thiazol-2-yl}-dimethyl-amine | ES/MS m/z 358 (M + 1)$^+$ |
| 9 | 7-(1-Ethyl-propyl)-2,5-dimethyl-3-(4-methyl-2-morpholin-4-yl-thiazol-5-yl)-pyrazolo[1,5-a]pyrimidine | ES/MS m/z 400 (M + 1)$^+$ |

*Use 6 eq of cesium carbonate.

Example 10

3-[4-Bromo-2-(2-methyl-2H-[1,2,4]triazol-3-yl)-thiazol-5-yl]-2,5-dimethyl-7-(1-propyl-butyl)-pyrazolo[1,5-a]pyrimidine

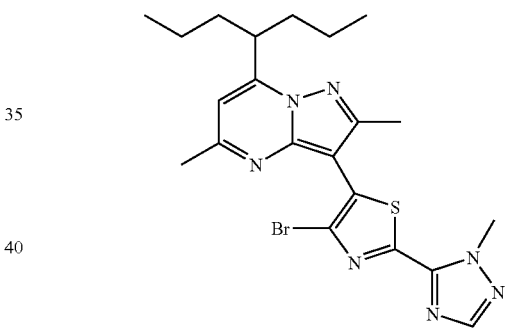

Charge an oven dried flask with 1-methyl-1,2,4-triazole (0.498, 6.00 mmol) and anhydrous THF (20 mL) and chill under an inert atmosphere to −78° C. Slowly add n-butyl lithium (2.5 M hexane solution, 2.4 mL, 6.0 mmol) and stir 30 min. Add anhydrous zinc chloride (1.36 g, 10.0 mmol) in one aliquot and stir 30 min at −78° C. Allow the reaction to warm to room temperature, stir 30 min, and add 3-(2,4-dibromothiazol-5-yl)-2,5-dimethyl-7-(1-propyl-butyl)-pyrazolo[1,5-a]pyrimidine (0.973 g, 2.00 mmol) and dichloro[1,1'-bis(diphenylphosphino)ferrocene]palladium (II) dichloromethane (0.163 g, 0.200 mmol). Reflux the reaction overnight in an oil bath (90° C.) under an inert atmosphere. Cool the reaction to room temperature, quench with water, and dilute with ethyl acetate (100 mL). Separate and extract the aqueous portion with dichloromethane (50 mL). Combine the organic phases, dry over anhydrous magnesium sulfate, filter, and concentrate under reduced pressure. Purify the resulting residue using flash chromatography, eluting with 100% hexane/0% (10% acetonitrile/40% THF/50% hexane) to 0% hexane/100% (10% acetonitrile/40% THF/50% hexane) in a step gradient of 10% increments to give a white solid (0.090 g, 9%). ES/MS m/z ($^{79}$Br) 487.7 (M+1)$^+$.

Alternate Preparation:

To a solution of 2,5-dimethyl-3-[2-(2-methyl-2H-[1,2,4]triazol-3-yl)-thiazol-5-yl]-7-(1-propyl-butyl)-pyrazolo[1,5-a]pyrimidine (6 g, 14.65 mmol) in acetonitrile (60 mL) add N-bromosuccinimide (2.74 g, 15.4 mmol) in one portion and stir at 22° C. for 10 h. Evaporate the solvent and dissolve the residue in a mixture of water (50 mL) and methyl-t-butyl ether (100 mL). Separate the organic layer and extract the aqueous layer with additional methyl-t-butyl ether (2×50 mL). Combine the organic portions and evaporate the solvent. Purify the resulting material by filtration through a silica gel pad, eluting with hexanes/ethyl acetate (3/1). Combine the product containing fractions and evaporate the solvent. Add heptanes (25 mL) and triturate the solid. Filter the solid and dry under vacuum to afford the title compound (5.5 g, 77%). ES/MS m/z ($^{79}$Br/$^{81}$Br) 488/490 (M+1)$^+$.

Example 10a

3-[4-Bromo-2-(2-methyl-2H-[1,2,4]triazol-3-yl)-thiazol-5-yl]-2,5-dimethyl-7-(1-propyl-butyl)-pyrazolo[1,5-a]pyrimidine, hydrochloride

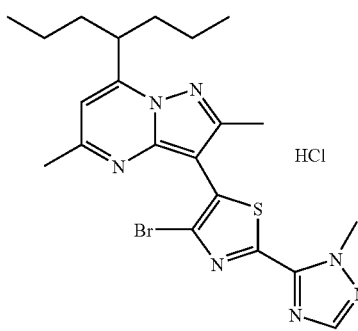

Dissolve 3-[4-bromo-2-(2-methyl-2H-[1,2,4]triazol-3-yl)-thiazol-5-yl]-2,5-dimethyl-7-(1-propyl-butyl)-pyrazolo[1,5-a]pyrimidine (750 mg, 1.54 mmol) in acetone (5 mL) and add 1 M HCl in diethyl ether (1.84 mL, 1.84 mmol). Stir the mixture at room temperature for 3 h and concentrate in vacuo. Dissolve the residue in diethyl ether/hexane=1/1 (5 mL) and crystallize the desired HCl salt (526 mg, 65%). ES/MS m/z ($^{81}$Br) 490 (M+1)$^+$; $^1$H-NMR(CDCl$_3$): 8.20 (s, 1H), 6.82 (s, 1H), 4.21 (s, 3H), 3.64 (m, 1H), 2.49 (m, 3H), 2.44 (s, 3H), 1.75 (m, 4H), 1.96(m, 4H), 0.81 (m, 6H).

Prepare the following compound essentially as described in Example 10.

| Ex. No. | Chemical name | Physical data |
|---|---|---|
| 11* | 7-(1-Ethyl-propyl)-2,5-dimethyl-3-[4-methyl-2-(2-methyl-2H-[1,2,4]triazol-3-yl)-thiazol-5-yl]-pyrazolo[1,5-a]pyrimidine | ES/MS m/z 396 (M + 1)$^+$ |

*Use 0.5 M zinc chloride in THF instead of anhydrous zinc chloride. Heat at 80° C. for 3 days.

Example 12

3-(4-Bromo-2-(2-methyl-2H-[1,2,4]triazol-3-yl)-thiazol-5-yl)-7-(1-ethyl-propyl)-2,5-dimethyl-pyrazolo[1,5-a]pyrimidine

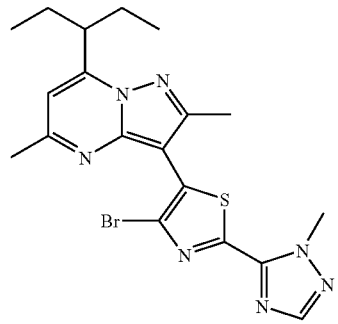

Under nitrogen atmosphere, add n-butyl lithium (2.5 M in hexane, 0.6 mL, 1.5 mmol) to a solution of 1-methyl-1,2,4-triazole (124.5 mg, 1 5 mmol) in THF (3 mL) at −78° C. and stir for 30 min. Add anhydrous zinc chloride (409 mg, 3 0 mmol), continue stirring for 30 min, warm up to room temperature and stir for 2 h. Add 3-(2,4-dibromo-thiazol-5-yl)-7-(1-ethyl-propyl)-2,5-dimethyl-pyrazolo[1,5-a]pyrimidine (229 mg, 0.5 mmol), followed by tetrakis(triphenylphosine)palladium (58 mg, 0.05 mmol) and reflux overnight. Cool to room temperature, dilute with ethyl acetate, and wash with saturated ammonia chloride. Dry the organic portion over sodium sulfate, filter, and concentrate to a residue. Purify the crude material by flash chromatography, eluting with hexanes:ethyl acetate (10:2.5) to give the title compound as a yellow foam (77 mg). MS (APCI) m/z ($^{79}$Br) 460.4 (M+1)$^+$.

Alternate Preparation from Example 21:

Add acetic acid (1 mL) and N-bromosuccinimide (4.1 g, 22 mmol) to a solution of 7-(1-ethyl-propyl)-2,5-dimethyl-3-[2-(2-methyl-2H-[1,2,4]triazol-3-yl)-thiazol-5-yl]-pyrazolo[1,5-a]pyrimidine (8 g, 21 mmol) in acetonitrile (80 mL). Stir the mixture 2 h at 22° C. Then evaporate the solvent and add water (50 mL) and methyl-t-butyl ether (100 mL) to the resulting residue. Separate the organic portion, dry over sodium sulfate, filter, and evaporate the solvent. Recrystallize the resulting residue from isopropyl alcohol to afford the title compound (8.7 g, 90%). ES/MS (m/z): ($^{79}$Br/$^{81}$Br) 460/462 (M+1)$^+$.

Example 12a 3-(4-Bromo-2-(2-methyl-2H-[1,2,4]triazol-3-yl)-thiazol-5-yl)-7-(1-ethyl-propyl)-2,5-dimethyl-pyrazolo[1,5-a]pyrimidine, p-toluene sulfonic acid Dissolve 3-(4-bromo-2-(2-methyl-2H-[1,2,4]triazol-3-yl)-thiazol-5-yl)-7-(1-ethyl-propyl)-2,5-dimethyl-pyrazolo[1,5-a]pyrimidine (50 mg, 0.109 mmol) in acetone (3 mL). Add a 0.25 M aqueous solution of p-toluene sulfonic acid (434.4 µL, 0.109 mmol) and evaporate the resulting mixture to dryness. Add ethyl acetate (12 mL) to get partial dissolution of the solids. Add methanol (1 mL) to achieve a clear solution. Concentrate the solution by slow evaporation until crystals are observed. Isolate the crystals by filtration and dry under vacuum at 25° C. to obtain about 50 mg of the title compound.

Determine the stoichiometry of the salt by ion chromatography using the following HPLC conditions: column: Phenomenex Phenosphere SAX, 4.6×150 mm at 30° C.; mobile phase: 50% acetonitrile/50% 0.025 M sodium phosphate buffer at pH=4.5; flow rate=1.5 mL/min; detection: UV at 205 nm; injection volume=5 μL; run time=3 min. Theoretical amount calc: 27.2% tosylate; found: 28.4% tosylate (average of three HPLC runs).

Example 13

{4-Chloro-5-[2,5-dimethyl-7-(1-propyl-butyl)-pyrazolo[1,5-a]pyrimidin-3-yl]-thiazol-2-yl}-dimethylamine Charge an oven dried flask with {4-bromo-5-[2,5-dimethyl-7-(1-propyl-butyl)-pyrazolo[1,5-a]pyrimidin-3-yl]-thiazol-2-yl-dimethylamine (0.20, 0.44 mmol) and anhydrous THF (3.0 mL) and chill under an inert atmosphere to −78° C. Slowly add n-butyl lithium (1.6 M hexane solution, 0.42 mL, 0.67 mmol) and stir 30 min. Add N-chlorosuccinimide (0.120 g, 0.889 mmol) in one aliquot and stir 30 min at −78° C. Allow the reaction to warm to room temperature, and stir for 5 h, checking the progress using LC/MS. Dilute with ethyl acetate (100 mL), wash with saturated ammonium chloride (50 mL), and back-extract the aqueous with dichloromethane (50 mL). Combine the organic phases, dry over anhydrous magnesium sulfate, filter, and concentrate under reduced pressure. Purify the resulting residue using flash chromatography, eluting with 100% hexane/0% (25% THF/hexane) to 0% hexane/100% (25% THF/hexane) in a step gradient of 10% increments to give a white solid (0.087 g, 48%). ES/MS m/z ($^{35}$Cl) 406.0 (M+1)$^+$.

Prepare the following examples essentially as described in Example 13 using the appropriate bromothiazole prepared above.

| Ex. No. | Chemical name | Physical data |
|---|---|---|
| 14 | 3-(4-Chloro-2-morpholin-4-yl-thiazol-5-yl)-2,5-dimethyl-7-(1-propyl-butyl)-pyrazolo[1,5-a]pyrimidine | ES/MS m/z ($^{35}$Cl) 448.0 (M + 1)$^+$ |
| 15 | {4-Chloro-5-[7-(1-ethyl-propyl)-2,5-dimethyl-pyrazolo[1,5-a]pyrimidin-3-yl]-thiazol-2-yl}-dimethyl-amine | MS (APCI) m/z ($^{35}$Cl) 378.0 (M + 1)$^+$ |

Preparation 18

2,4-dichlorothiazole

Cool to 5° C. a mixture of thiazolidine-2,4-dione (50 g, 0.43 mol) in phosphorus oxychloride (240 mL) and add pyridine (34 mL, 0.43 mol) over 15 min. Heat the mixture to 125° C. for 4 h and then cool to 22° C. Remove the excess phosphorus oxychloride by vacuum distillation and add the residue to water (1 L) chilled to a temperature of 5° C. Extract the mixture with methylene chloride (3×400 mL). Combine the organic portions and evaporate the solvent to afford the title compound (50 g, 76%). EI/MS m/z: ($^{35}$Cl$^{35}$Cl/$^{35}$Cl$^{37}$Cl/$^{37}$Cl$^{37}$Cl) 153/155/157 (M+1)$^+$.

Preparation 19

4-chloro-2-morpholino-thiazole

To a mixture of 2,4-dichlorothiazole (34 g, 0.22 mol) in acetonitrile (425 mL) add potassium carbonate (60.9 g, 0.44 mol) and then morpholine (21.2 mL, 0.225 mol) dropwise over 30 min. Reflux the mixture at 40° C. and then cool to 22° C. Filter the mixture and evaporate the filtrate. Triturate the residue with i-propyl alcohol (60 mL) at 22° C. for one hour. Filter the solids and dry under vacuum to a constant weight to afford the title compound (34.5 g, 76%). ES/MS m/z ($^{35}$Cl) 205 (M+1)$^+$.

Example 16

3-(4-Chloro-2-morpholin-4-yl-thiazol-5-yl)-7-(1-ethyl-propyl)-2,5-dimethyl-pyrazolo[1,5-a]pyrimidine

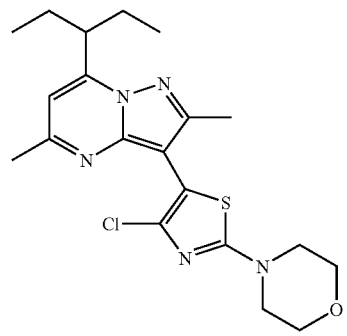

Under a nitrogen atmosphere dissolve 3-(4-bromo-2-morpholin-4-yl-thiazol-5-yl)-7-(1-ethyl-propyl)-2,5-dimethyl-pyrazolo[1,5-a]pyrimidine (116 mg, 0.25 mmol) in THF (1.5 mL) and chill to −78° C. Add n-butyl lithium (0.1 mL. 2.5 M in hexane, 0.25 mmol) and stir at −78° C. for 30 min. Add N-chlorosuccinimide (33.4 mg, 0.25 mmol) and stir for another 30 min, slowly warming to room temperature. After stirring overnight, quench the reaction by adding a solution of saturated ammonia chloride and extract with ethyl acetate. Wash the organic layer with brine, dry over sodium sulfate, filter, and concentrate to a residue. Purify the crude material by flash chromatography, eluting with hexanes:dichloromethane:ethyl acetate (5:5:2) to provide the title compound (54 mg). MS (APCI) m/z ($^{35}$Cl) 420.6 (M+1)$^+$; $^1$H NMR (400 MHz, CDCl$_3$): 6.44 (s, 1H), 3.79 (t, 4H, J=4.8 Hz), 3.63-3.56 (m, 1H), 3.47 (t, 4H, J=4.8 Hz), 2.55 (s, 3H), 2.45 (s, 3H), 1.88-1.75 (m, 4H), 0.87 (t, 6H, J=7.5 Hz).

Alternate Preparation from Preparation 6:

Combine 7-(1-ethyl-propyl)-3-iodo-2,5-dimethyl-pyrazolo[1,5-a]pyrimidine, (9 g, 26.2 mmol) and 4-chloro-2-morpholino-thiazole (7.5 g, 36 7 mmol) in dimethylformamide (90 mL) previously degassed with nitrogen. Add cesium carbonate (17.8 g, 55 mmol), copper iodide (250 mg, 1.31 mmol), triphenylphosphine (550 mg, 2.09 mmol) and palladium acetate (117 mg, 0.52 mmol). Heat the mixture to 125° C. for 16 h and then cool to 22° C. Add water (900 mL) and extract with methyl-t-butyl ether (3×200 mL). Combine the organic portions and evaporate the solvent. Purify by silica gel chromatography eluting with hexanes/ethyl acetate (4/1) to afford the title compound (6.4 g, 62%). ES/MS m/z ($^{35}$Cl) 420 (M+1)$^+$.

Example 16a 3-(4-Chloro-2-morpholin-4-yl-thiazol-5-yl)-7-(1-ethyl-propyl)-2,5-dimethyl-pyrazolo[1,5-a]pyrimidine, hydrochloride Dissolve 3-(4-chloro-2-morpholin-4-yl-thiazol-5-yl)-7-(1-ethyl-propyl)-2,5-dimethyl-pyrazolo[1,5-a]pyrimidine (1.40 g, 3.33 mmol) in acetone (10 mL) at 50° C. and cool to room temperature. Add hydrogen chloride (2 M in diethyl ether, 2.0 mL, 4.0 mmol) and stir well in a sonicator. Concentrate the solution a little and add a minimal amount of diethyl ether to crystallize the HCl salt. Cool the mixture in a refrigerator overnight. Add additional hydrogen chloride (2 M in diethyl ether, 2.0 mL, 4 0 mmol) and cool in a refrigerator. Filter the crystalline material and dry to obtain the title compound (1.15 g, 75%). ES/MS m/z ($^{35}$Cl) 420 (M+1)$^+$; $^1$H NMR(CDCl3): 9.18 (br, 1H), 6.86 (s, 1H), 3.72 (m, 4H), 3.49(m, 1H), 3.39 (m, 4H), 2.48 (s, 3H), 2.38(s, 3H), 1.79 (m, 4H), 0.79 (m, 6H).

Example 17

3-(4-Bromo-2-butyl-thiazol-5-yl)-7-(1-ethyl-propyl)-2,5-dimethyl-pyrazolo[1,5-a]pyrimidine Under a nitrogen atmosphere, add n-butyl lithium (2.5 M in hexane, 0.2 mL, 0.5 mmol) to a solution of 3-(2,4-dibromo-thiazol-5-yl)-7-(1-ethyl-propyl)-2,5-dimethyl-pyrazolo[1,5-a]pyrimidine (230 mg, 0.5 mmol) in THF (3 mL) at −78° C. After 30 min, add 1-iodobutane (138 mg, 0.75 mmol) and continue stirring for 1 hour. Warm up to room temperature and stir for one hour. Quench the reaction by adding saturated ammonia chloride solution and extract with ethyl acetate. Dry the organic portion over sodium sulfate, filter, and concentrate to a residue. Purify the crude material by flash chromatography, eluting with hexanes/ethyl acetate (10/1.5) to give the title compound as orange foam (78 mg). ES/MS m/z ($^{81}$Br) 437.4 (M+1)$^+$.

Prepare the following example essentially as described in Example 17.

| Ex. No. | Chemical name | Physical data |
| --- | --- | --- |
| 18 | 3-(4-Bromo-2-methoxymethyl-thiazol-5-yl)-7-(1-ethyl-propyl)-2,5-dimethyl-pyrazolo[1,5-a]pyrimidine- | MS (APCI) m/z ($^{81}$Br) 424.6 (M + 1)$^+$ |

Example 19

7-(1-Ethyl-propyl)-3-(2-methoxymethyl-thiazol-5-yl)-2,5-dimethyl-pyrazolo[1,5-a]pyrimidine Under a nitrogen atmosphere, add n-butyl lithium (2.5 M in hexane, 0.4 mL, 1.0 mmol) to a solution of 7-(1-ethyl-propyl)-2,5-dimethyl-3-thiazol-5-yl-pyrazolo[1,5-a]pyrimidine (300 mg, 1.0 mmol) in THF (3 mL) at −78° C. Stir 30 min and add 1-iodomethyl methyl ether (205 mg, 1.2 mmol). Continue stirring for one hour and then slowly warm up to room temperature and stir overnight. Quench the reaction by adding saturated ammonium chloride solution and extract with ethyl acetate. Wash the organic layer with brine, dry over sodium sulfate, filter, and concentrate under vacuum to a residue. Purify the crude material by flash chromatography, eluting with hexanes/ethyl acetate (10/2) to give the title compound as a yellow foam (184 mg). MS (APCI) m/z 345.3 (M+1)$^+$.

Example 20

3-(4-Chloro-2-methoxymethyl-thiazol-5-yl)-7-(1-ethyl-propyl)-2,5-dimethyl-pyrazolo[1,5-a]pyrimidine Add n-butyl lithium (2.5 M in hexanes, 174 mL, 0.43 mmol) to a stirred solution of 7-(1-ethyl-propyl)-3-(2-methoxymethyl-thiazol-5-yl)-2,5-dimethyl-pyrazolo[1,5-a]pyrimidine (150 mg, 0.43 mmol) in THF (3 mL) at −78° C. Stir for 30 min and add N-chlorosuccinimide (87 mg, 0.653 mmol). Stir 30 min and then warm the reaction slowly to room temperature allowing the reaction to continue overnight. Quench the reaction by adding saturated ammonium chloride solution, extract with ethyl acetate, dry over sodium sulfate, filter, and concentrate to a residue. Purify by flash chromatography, eluting with hexanes/ethyl acetate (10/2) to give the title compound (7 mg). MS (APCI) m/z ($^{35}$Cl) 379.3 (M+1)$^+$.

Example 21

7-(1-Ethyl-propyl)-2,5-dimethyl-3-[2-(2-methyl-2H-[1,2,4]triazol-3-yl)-thiazol-5-yl)-pyrazolo[1,5-a]pyrimidine Mix 3-(4-bromo-2-(2-methyl-2H-[1,2,4]triazol-3-yl)-thiazol-5-yl)-7-(1-ethyl-propyl)-2,5-dimethyl-pyrazolo[1,5-a]pyrimidine (175 mg, 0.38 mmol) and copper(I) chloride (132 mg, 1.33 mmol) in DMF (5 mL) and heat to 120° C. for 24 h. Cool to room temperature, dilute with ethyl acetate, and wash with brine. Dry the organic layer over sodium sulfate, filter, and concentrate under vacuum to a residue. Purify by flash chromatography, eluting with hexanes and then hexanes/EtOAc (10/1.8) to give a yellow-orange solid (45 mg). ES/MS m/z 382.0 (M+1)$^+$.

Alternate Preparation:

Add n-butyl lithium (2.5 M in hexanes, 57.6 mL, 144 mmol) to a solution of N-methyltriazole (11.95 g, 144 mmol) in THF (600 mL) at −78° C. under a nitrogen atmosphere, keeping the temperature below −74° C. during the addition. Then add zinc chloride, dry powder, (26 g, 192 mmol) in one portion and warm the mixture to 22° C. in one hour. Add 7-(1-ethyl-propyl)-3-(2-iodo-thiazol-5-yl)-2,5-dimethyl-pyrazolo[1,5-a]pyrimidine (12.5 g, 29 mmol) and tetrakis (triphenyl)phosphine palladium catalyst (1.15 g, 0.01 mol) in one portion and heat the mixture to reflux under nitrogen for 8 h. Cool the mixture to 22° C. and add water (300 mL). Separate the organic layer and extract the aqueous layer with methyl-t-butyl ether (2×200 mL). Combine the organic portions, dry over sodium sulfate, filter, and evaporate the solvent. Purify by passing over a silica gel pad eluting with hexanes/ethyl acetate (4/1) to afford the title compound (8 g, 72%). ES/MS m/z 382 (M+1)$^+$.

Example 22

3-(4-Chloro-2-(2-methyl-2H-[1,2,4]triazol-3-yl)-thiazol-5-yl)-7-(1-ethyl-propyl)-2,5-dimethyl-pyrazolo[1,5-a]pyrimidine Stir a mixture of 7-(1-ethyl-propyl)-2,5-dimethyl-3-[2-(2-methyl-2H-[1,2,4]triazol-3-yl)-thiazol-5-yl)-pyrazolo[1,5-a]pyrimidine (20 mg, 0.052 mmol) and N-chlorosuccinimide (7.6 mg, 0.0569 mmol) in dichloromethane (0.5 mL) and acetonitrile (0.5 mL) at room temperature overnight in a vial. Concentrate to a residue. Purify by flash chromatography, eluting with hexanes and then with hexanes/ethyl acetate (10/1.5) to give the title compound (16 mg). ES/MS m/z ($^{35}$Cl) 416.0 (M+1)$^+$.

Example 23

7-(1-Ethyl-propyl)-3-(4-methoxy-2-morpholin-4-yl-thiazol-5-yl)-2,5-dimethyl-pyrazolo[1,5-a]pyrimidine Stir a mixture of 3-(4-bromo-2-morpholin-4-yl-thiazol-5-yl)-7-(1-ethyl-propyl)-2,5-dimethyl-pyrazolo[1,5-a]pyrimidine (162 mg, 0.35 mmol), sodium methoxide (57 mg, 1.05 mmol) and copper(I) iodide (67 mg, 0.35 mmol) in methanol (3 mL) in a sealed 4-mL vial for 15 h at 120° C. Cool to room temperature, remove the solid by filtration, and concentrate the filtrate under vacuum. Purify the residue by flash chromatography, eluting with hexanes/THF (10/2). Recrystallize the material from methanol to give the title compound (20 mg). ES/MS m/z 416.0 (M+1)$^+$.

Preparation 20

4-Bromo-5-[7-(1-ethyl-propyl)-2,5-dimethyl-pyrazolo[1,5-a]pyrimidin-3-yl]-thiazole-2-carbaldehyde Under a nitrogen atmosphere, add n-butyl lithium (1.6 M in hexanes, 0.312 mL, 0.50 mmol) to a THF solution (2.5 mL) of 3-(2,4-dibromo-thiazol-5-yl)-7-(1-ethyl-propyl)-2,5-dimethyl-pyrazolo[1,5-a]pyrimidine (230 mg, 0.50 mmol) at −78° C. and stir for 30 min. Add a THF (0.5 mL) solution of N-formyl morpholine (58 mg, 0.50 mmol). Stir for one hour, then store the reaction at −20° C. overnight. Warm the reaction to room temperature, dilute with ether, and quench by adding 4 N HCl (4 mL). Separate and extract the organic phase with 4 N HCl (2×4 mL). Combine the aqueous portions, treat with solid sodium bicarbonate to pH=8 to 9 and then extract with diethyl ether. Combine all the organic layers, wash with brine, dry over sodium sulfate, filter, and concentrate to a residue. Purify the crude material by flash chromatography, eluting with hexanes/dichloromethane/ethyl acetate (5/5/1) to give the title compound (154 mg). MS (APCI) m/z ($^{81}$Br) 409.0 (M+1)$^+$.

Example 24

3-(4-Bromo-2-morpholin-4-yl-methyl-thiazol-5-yl)-7-(1-ethyl-propyl)-2,5-dimethyl-pyrazolo[1,5-a]pyrimidine Combine 4-bromo-5-[7-(1-ethyl-propyl)-2,5-dimethyl-pyrazolo[1,5-a]pyrimidin-3-yl]-thiazole-2-carbaldehyde (150 mg, 0.368 mmol), morpholine (35 mg, 0.405 mmol) and sodium triacetoxyborohydride (97 mg, 0.46 mmol), in dichloromethane (3 mL) and methanol (0.5 mL). Stir overnight, add additional morpholine (35 mg, 0.405 mmol), and sodium triacetoxyborohydride (97 mg, 0.46 mmol), and stir 4 h more. Remove the solvent under vacuum, dilute with dichloromethane, and wash with brine. Dry the organic phase over sodium sulfate, filter, and concentrate under vacuum. Purify the resulting material using flash chromatography, eluting with dichloromethane:2 M ammonia in methanol (10:1) to give a mixture. Purify the mixture using a reverse phase column, eluting with water/acetonitrile (80/20) to water/acetonitrile (10/90) to give the title compound (20 mg). ES/MS m/z ($^{81}$Br) 480.0 (M+1)$^+$.

Example 25

3-(4-Bromo-2-pyridin-4-yl-thiazol-5-yl)-7-(1-ethyl-propyl)-2,5-dimethyl-pyrazolo[1,5-a]pyrimidine Under a nitrogen atmosphere, add n-butyl lithium (1.6 M in hexane, 0.312 mL, 0.5 mmol) to a solution of 3-(2,4-dibromo-thiazol-5-yl)-7-(1-ethyl-propyl)-2,5-dimethyl-pyrazolo[1,5-a]pyrimidine (229 mg, 0.5 mmol) in THF (4 mL) at −78° C. After stirring for 30 min, add anhydrous zinc chloride (264 mg, 1 5 mmol) and continue stirring for 30 min. Warm the reaction to room temperature and stir for one hour. Add 4-iodopyridine (103 mg, 0.5 mmol), followed by 1,1'-bis(diphenylphosphino)ferrocene palladium (II) chloride (dichloromethane adduct) (0.40.8 mg, 0.05 mmol). Heat the reaction to reflux overnight. Cool to room temperature, dilute with ethyl acetate, and wash with water and brine. Dry the organic layer over sodium sulfate, filter, and concentrate to a residue. Purify the crude material by flash chromatography, eluting with dichloromethane:2 N ammonia in methanol (10:0.75) to give a mixture. Purify the mixture using a reverse phase column, eluting with water: acetonitrile=80:20 to water: acetonitrile=10:90, to give the title compound (19 mg). ES/MS m/z ($^{79}$Br) 456.0 (M+1)$^+$.

Preparation 21

4-Trifluoromethyl-thiazole-2-ylamine

Add thiourea (4.0 g, 52.3 mmol) and 3-bromo-1,1,1-trifluoropropan-2-one (5.5 mL, 10 g, 52.3 mmol) to ethanol (100 mL) and heat at 50° C. for 2 h. Cool to room temperature and concentrate to dryness. Dissolve the residue in water and adjust the pH to >12 with 2 M NaOH. Extract with diethyl ether (4×). Dry the combined organic extracts with sodium sulfate, filter, and concentrate under vacuum. Purify the resulting material by silica gel chromatography (CH$_2$Cl$_2$) to obtain the title compound (6.9 g, 79%). ES/MS m/z 169 (M+1)$^+$.

Preparation 22

5-Bromo-4-trifluoromethyl-thiazol-2-ylamine, hydrobromide

Add bromine (2.0 mL, 6.28 g, 39.3 mmol) dropwise to an ice-bath cooled solution of 4-trifluoromethyl-thiazole-2-ylamine (6.0 g, 35.7 mmol) in diethyl ether (60 mL). Stir for one hour after the addition is complete and then warm to room temperature. Collect the solids by filtration and wash with diethyl ether to obtain the title compound (10.5 g, 90%). ES/MS m/z ($^{79}$Br/$^{81}$Br) 247/249 (M+1)$^+$.

Preparation 23

5-Bromo-2-(2,5-dimethyl-pyrrol-1-yl)-4-trifluoromethyl-thiazole

Add hexane-2,5-dione (3.5 mL, 3.4 g, 30 2 mmol) to a solution of 5-bromo-4-trifluoromethyl-thiazol-2-ylamine hydrobromide (9.0 g, 27.4 mmol) in methanol (60 mL). Stir at room temperature overnight. Add phosphate buffer (50 mL, pH=7). Collect the resulting precipitate by filtration, washing with water. Dissolve the filter cake in CH$_2$Cl$_2$ and dry over sodium sulfate. Filter and concentrate under vacuum to obtain the title compound (8.2 g, 92%). $^1$H NMR (400 MHz, CDCl$_3$) δ 5.91 (s, 2H), 2.27 (s, 6H).

Example 26

3-[2-(2,5-Dimethyl-pyrrol-1-yl)-4-trifluoromethyl-thiazol-5-yl]-7-(1-ethyl-propyl)-2,5-dimethyl-pyrazolo[1,5-a]pyrimidine

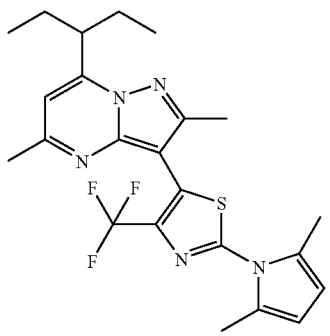

Cool a solution of 5-bromo-2-(2,5-dimethyl-pyrrol-1-yl)-4-trifluoromethyl-thiazole (2.2 g, 6.6 mmol) in THF (25 mL) in a dry ice bath. Add t-butyl lithium (1.7 M in pentane, 8.5 mL, 14.5 mmol) dropwise. Stir for 45 min and then add zinc chloride (0.5 M in THF, 14.6 mL, 7.3 mmol) dropwise. Stir 5 min and remove the cooling bath. Stir 30 min and then add 7-(1-ethyl-propyl)-3-iodo-2,5-dimethyl-pyrazolo[1,5-a]pyrimidine (1.5 g, 4.4 mmol) and bis(tri-t-butylphosphine)palladium (0) (450 mg, 0.9 mmol). Reflux for 24 h. Cool the reaction, pour the mixture into diethyl ether, and wash with water (2×). Extract the combined water layers with diethyl ether. Dry the combined organic portions over sodium sulfate, filter, and concentrate to dryness under vacuum. Purify the resulting residue by silica gel chromatography (75-100% $CH_2Cl_2$ in hexanes) to give the title compound (1.47 g, 72%). HR-ToF-MS m/z calcd for $C_{23}H_{26}F_3N_5S+H^+$: 462.1939, found: 462.1915.

Example 27

5-[7-(1-Ethyl-propyl)-2,5-dimethyl-pyrazolo[1,5-a]pyrimidin-3-yl]-4-trifluoromethyl-thiazol-2-ylamine Add hydroxylamine (2 mL, 50% in water) to a solution of 3-[2-(2,5-dimethyl-pyrrol-1-yl)-4-trifluoromethyl-thiazol-5-yl]-7-(1-ethyl-propyl)-2,5-dimethyl-pyrazolo[1,5-a]pyrimidine (1.1 g, 2.3 mmol) in acetic acid (10 mL). Heat the reaction to 80° C. for 6 h. Cool to room temperature. Pour into diethyl ether and wash with 2 M NaOH (2×) and then once with water. Dry the organic portion over sodium sulfate, filter, and concentrate to dryness under vacuum. Purify the resulting residue by silica gel chromatography (40% ethyl acetate in hexanes) to give the title compound (0.76 g, 87%). ES/MS m/z 384 (M+1)⁺.

Preparation 24

3-(2-Bromo-4-trifluoromethyl-thiazol-5-yl)-7-(1-ethyl-propyl)-2,5-dimethyl-pyrazolo[1,5-a]pyrimidine Heat a mixture of copper(II) bromide (540 mg, 2.4 mmol) and t-butylnitrite (0.36 mL, 310 mg, 3.0 mmol) in acetonitrile (20 mL) to 60° C. Add 5-[7-(1-ethyl-propyl)-2,5-dimethyl-pyrazolo[1,5-a]pyrimidin-3-yl]-4-trifluoromethyl-thiazol-2-ylamine (755 mg, 2.0 mmol) as a solid. Heat the reaction to 80° C. for 2 h. Cool the reaction, pour into diethyl ether and extract with water (3×). Dry the organic layer over sodium sulfate, filter, and concentrate to dryness under vacuum. Purify the resulting residue by silica gel chromatography in $CH_2Cl_2$ to give the title compound (0.77 g, 87%). ES/MS m/z ($^{79}$Br/$^{81}$Br) 447, 449 (M+1)⁺.

Example 28

{5-[7-(1-Ethyl-propyl)-2,5-dimethyl-pyrazolo[1,5-c]pyrimidin-3-yl]-4-trifluoromethyl-thiazol-2-yl}-dimethyl-amine Heat a sealed tube containing 3-(2-bromo-4-trifluoromethyl-thiazol-5-yl)-7-(1-ethyl-propyl)-2,5-dimethyl-pyrazolo[1,5-a]pyrimidine (313 mg, 0.7 mmol), and dimethyl amine (2 M in THF, 4 mL, 8 mmol) in methanol (4 mL) to 80° C. for 2 h. Cool the reaction and concentrate under vacuum. Purify the resulting residue by silica gel chromatography, eluting with 0-30% ethyl acetate in $CH_2Cl_2$, to give the title compound (0.28 g, 97%). HR-ToF-MS m/z calcd for $C_{19}H_{24}F_3N_5S+H^+$ 412.1770, found: 412.1783.

Prepare the following example essentially as described for Example 28 with the exception that the reaction is refluxed for 8 h.

| Ex. No. | Chemical name | Physical data |
|---|---|---|
| 29 | 7-(1-Ethyl-propyl)-2,5-dimethyl-3-(2-morpholin-4-yl-4-trifluoromethyl-thiazol-5-yl)-pyrazolo[1,5-a]pyrimidine | HR-ToF-MS m/z calcd for $C_{21}H_{26}F_3N_5OS + H^+$: 454.1873, found: 454.1888 |

Example 30

N-{5-[7-(1-Ethyl-propyl)-2,5-dimethyl-pyrazolo[1,5-c]pyrimidin-3-yl]-4-trifluoromethyl-thiazol-2-yl}-acetamide Add hydroxylamine (50% in water, 5 mL,) to a solution of 3-[2-(2,5-dimethyl-pyrrol-1-yl)-4-trifluoromethyl-thiazol-5-yl]-7-(1-ethyl-propyl)-2,5-dimethyl-pyrazolo[1,5-a]pyrimidine (2.4 g, 5.2 mmol) in acetic acid (25 mL). Heat the reaction to 80° C. for 72 h. Cool the reaction to room temperature, pour into diethyl ether and wash with 2 M NaOH (2×) and then once with water. Dry the organic portion over sodium sulfate, filter, and concentrate to dryness. Purify the resulting residue by column chromatography, eluting with 40% ethyl acetate in hexanes to give the title compound (0.28 g, 13%). HR-ToF-MS m/z calcd for $C_{19}H_{22}F_3N_5OS+H^+$ 426.1575, found: 426.1565.

Example 31

(2-{5-[7-(1-Ethyl-propyl)-2,5-dimethyl-pyrazolo[1,5-a]pyrimidin-3-yl]-4-trifluoromethyl-thiazol-2-ylamino}-ethyl)-carbamic acid tert-butyl ester

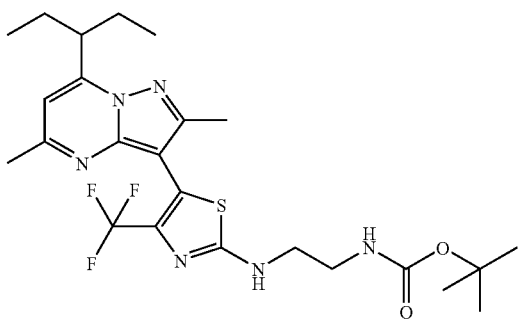

Add (2-amino-ethyl)-carbamic acid tert-butyl ester (0.5 mL, 506 mg, 3.2 mmol) to a solution of 3-(2-bromo-4-trifluoromethyl-thiazol-5-yl)-7-(1-ethyl-propyl)-2,5-dimethyl-pyrazolo[1,5-a]pyrimidine (100 mg, 0.22 mmol) and triethylamine (0.3 mL, 222 mg, 2.2 mmol) in methanol (1 mL). Evaporate off the methanol and heat to 80° C. overnight. Cool the reaction to room temperature and concentrate under vacuum. Purify the resulting residue by column chromatography, eluting with 10-50% ethyl acetate in $CH_2Cl_2$, to give the title compound (0.11 g, 97%). ES/MS m/z 527.2 (M+1)$^+$.

Prepare the compounds below as essentially described in Example 31 using the appropriate amine

| Prep. or Ex. No. | Chemical name | Physical data |
|---|---|---|
| Prep. 25* | [2-({5-[7-(1-ethyl-propyl)-2,5-dimethyl-pyrazolo[1,5-a]pyrimidin-3-yl]-4-trifluoro-methyl-thiazol-2-yl}-propyl-amino)-ethyl]-carbamic acid tert-butyl ester | ES/MS m/z 569.3 (M + 1)$^+$ |
| Prep. 26** | (S)-(1-{5-[7-(1-ethyl-propyl)-2,5-dimethyl-pyrazolo[1,5-a]pyrimidin-3-yl]-4-trifluoromethyl-thiazol-2-yl}-pyrrolidin-3-yl)-carbamic acid tert-butyl ester | ES/MS m/z 553.3 (M + 1)$^+$ |
| Ex. 32*** | N-{5-[7-(1-Ethyl-propyl)-2,5-dimethyl-pyrazolo[1,5-a]pyrimidin-3-yl]-4-trifluoro-methyl-thiazol-2-yl}-N,N'-dipropyl-ethane-1,2-diamine, hydrochloride | ES/MS m/z 511.2 (M + 1)$^+$ |

*Heat at reflux in EtOH overnight. Evaporate EtOH and heat at 110° C. for 24 h.
**Heat at 80° C. in EtOH overnight.
***Make the HCl salt and recrystallize from EtOAc/hexanes.

Example 33

$N^1$-{5-[7-(1-Ethyl-propyl)-2,5-dimethyl-pyrazolo[1,5-a]pyrimidin-3-yl]-4-trifluoromethyl-thiazol-2-yl}-ethane-1,2-diamine, hydrochloride Add (2-{5-[7-(1-ethyl-propyl)-2,5-dimethyl-pyrazolo[1,5-a]pyrimidin-3-yl]-4-trifluoromethyl-thiazol-2-ylamino}-ethyl)-carbamic acid tert-butyl ester (101 mg, 0.192 mmol) to 1 M HCl in methanol (1 mL). Heat the reaction at 70° C. overnight. Cool the reaction and concentrate under vacuum from methanol/ethyl acetate. Triturate the resulting residue with ethyl acetate to obtain the title compound (64 mg, 78%). ES/MS m/z 427.0 (M+1)$^+$.

Prepare the following examples essentially as described for Example 33.

| Ex. No. | Chemical name | Physical data |
|---|---|---|
| 34 | $N^1$-{5-[7-(1-Ethyl-propyl)-2,5-dimethyl-pyrazolo[1,5-a]pyrimidin-3-yl]-4-trifluoromethyl-thiazol-2-yl}-$N^1$-propyl-ethane-1,2-diamine, hydrochloride | ES/MS m/z 469.2 (M + 1)$^+$ |
| 35 | (S)-1-{5-[7-(1-Ethyl-propyl)-2,5-dimethyl-pyrazolo[1,5-a]pyrimidin-3-yl]-4-trifluoromethyl-thiazol-2-yl}-pyrrolidin-3-ylamine, hydrochloride | ES/MS m/z 453.0 (M + 1)$^+$ |

Example A

In Vivo Potency Assessment Using Ex Vivo Binding

To assess in vivo potency, a compound of the present invention is evaluated using ex vivo binding. Using the procedures as provided in D. R. Gehlert et al., *EJP* 509: 145-153 (2005), a compound is administered to a rat via the oral route. The binding of $^{125}$I-sauvagine to the cerebellum is then assessed ex vivo as described in Gehlert et al. For example, Example 15 provides 65% inhibition at 10 mg/kg.

Example B

CRF1 Filter Binding Assay

The limitations of plasmid-based human CRF1 expression, in terms of generating a recombinant cell line with sufficient receptor density to develop a binding assay, are overcome by using a Phoenix retroviral expression system licensed from Stanford. The stable HEK-hCRF1 cell line is used to prepare membranes and binding reactions (200 μL) are set up as follows: 50 μL of $^{125}$I-sauvagine (0.2 nM final), 50 μL compound and 100 μL CRF1 membrane (25 μg/reaction). The reactions are incubated at room temperature for 2 h and then terminated by filtration through pre-treated FB Millipore glass fiber filter plates (96 well). The plates are washed twice with ice-cold assay buffer (50 mM tris, 12.5 mM NaCl, 1 mM EDTA, 10 mM $MgCl_2$, 0.05% BSA, pH 7.2), air dried over night and counted with 100 μL Microscint 40 in a MicroBeta counter. Non-specific binding (NSB) is determined in the presence of 0.5 μM non-labeled sauvagine. Triplicate determinations are typically run and the median data points plotted by Graph Pad Prism.

Using this assay, the exemplified compounds of the present invention inhibit the binding of $^{125}$I-Sauvagine (4 nM) in roller/adherent cells with a Ki (inhibition constant) below 1 μM. For example, Example 15 exhibits a Ki of 6.2 nM.

Example C

CRF2 Filter Binding Assay

The limitations of plasmid-based human CRF2 expression, in terms of generating a recombinant cell line with sufficient receptor density to develop a binding assay, are overcome by using a Phoenix retroviral expression system licensed from Stanford. The stable HEK-hCRF2 cell line is used to prepare membranes and binding reactions (200 μL) are set up as follows: 50 μL of $^{125}$I-sauvagine (0.2 nM final concentration), 50 μL compound and 100 μL CRF2 membrane (25 μg/reaction). The reactions are incubated at room temperature for 2 hours and then terminated by filtration through pre-treated FB Millipore glass fiber filter plates (96 well). The plates are washed twice with ice-cold assay buffer (50 mM tris, 12.5 mM NaCl, 1 mM EDTA, 10 mM $MgCl_2$, 0.05% BSA, pH 7.2), air dried over night and counted with 100 µL Microscint 40 in a MicroBeta counter. Non-specific binding (NSB) is determined in the presence of 0.5 µM non-labeled sauvagine. Alternatively, compounds are evaluated using a Scintillation Proximity assay. This assay is set up as follows: 50 µL of $^{125}$I-Sauvagine (0.2 nM final concentration), 50 µL compound or non-labelled sauvagine (NSB) and 100 µL containing 250 µg wheat germ agglutinin (WGA) SPA beads and CRF2 membrane (1.5 µg/reaction). Plates are incubated for 4-5 h at room temperature and then centrifuged at 200×g for 10 min. Bound radioactivity is assessed using a Wallac Trilux scintillation counter. Binding is assessed typically using triplicate determinations and the median data points plotted by Graph Pad Prism. Compounds are initially screened at a fixed concentration and, if sufficient activity is noted, subsequent concentration-response curves are generated.

Particular exemplified compounds of the present invention are tested in the CRF2 binding assay and exhibit weak affinity for the CRF2 receptor. For example, Example 15 exhibits 11% inhibition at a concentration of 50 µM. This result suggests that the compounds of the present invention are selective for the CRF1 receptor, (relative to CRF2).

Example D

Bioavailability and Pharmacokinetic Properties

The volume of distribution (Vdist) relates the amount of the drug in the body to the concentration of the drug in the blood or plasma. The volume of distribution refers to the fluid volume that would be required to contain the total amount of the drug in the body at the same concentration as in the blood or plasma: Vdist=amount of drug in the body/concentration of drug in blood or plasma (Goodman and Gillman's). For a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, Vdist can be used to determine a loading dose to achieve a steady state concentration.

To test for volume of distribution, Male Sprague Dawley rats (N=3) are administered a single 1 mg/kg intravenous dose of compound. Multiple plasma samples are collected at time points from 0.08 to 24 hours post-dose. The plasma samples are analyzed by LC/MS/MS to determine the plasma concentrations. Plasma pharmacokinetic calculations are performed to determine the pharmacokinetic parameters including Vdist and plasma clearance (Clp).

Compounds of the present invention preferably have favorable bioavailability profiles. For example, a majority of commercial CNS and cardiovascular drugs exhibit a human Vdist of <10 L/Kg. In comparison with CRF antagonists, CP154526 (Schulz et al., *Proc. Natl. Acad. Sci.* (*USA*), 93:10477 (1996)) and NBI30775 (Chen et al., *Drug Development Research*, 65:216 (2005)), which exhibit a rat Vdist of 114 L/Kg and 76 L/Kg, respectively, when analyzed separately. Example 15 of the present invention, when analyzed separately, exhibits a rat Vdist of only 7.2 L/Kg following a single intravenous dose of 1 mg/kg.

Further, the plasma clearance (CLp) is a measure of the rate of removal of the drug from the body. Following an intravenous dose and first-order kinetics, the plasma clearance may be determined using the following equation: CLp=Dose/AUC, where AUC is the total area under the curve that describes the concentration of the drug in the plasma as a function of time from zero to infinity. Reference CRF antagonists CP154526 and NBI37582 exhibit rat clearance (CLp) of 83 and 306 mL/min/kg, respectively, when analyzed separately, following a single intravenous dose, while Example 15 of the present invention, when analyzed separately, exhibits a rat CLp of only 23.6 mL/min/kg.

We claim:
1. A compound of Formula I

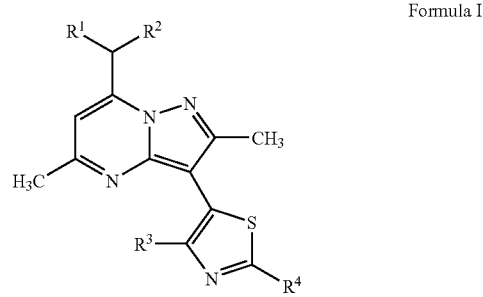

Formula I wherein:
$R^1$ and $R^2$ are independently ethyl or n-propyl;
$R^3$ is hydrogen, Cl, Br, methyl, trifluoromethyl or methoxy;
$R^4$ is hydrogen, Br, $R^aR^bN$—, methoxymethyl, n-butyl, acetamido, pyridin-4-yl, morpholin-4-yl,

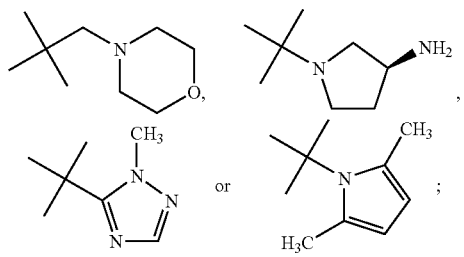

or $R^a$ and $R^b$ are independently hydrogen, $C_1$-$C_3$alkyl, $H_2NCH_2CH_2$—, $(CH_3)_3COC(O)NHCH_2CH_2$—, or $CH_3CH_2CH_2NHCH_2CH_2$—;
or a pharmaceutically acceptable salt thereof.

2. The compound according to claim 1, or a pharmaceutically acceptable salt thereof, wherein $R^3$ is Cl, Br, methyl or trifluoromethyl.

3. The compound according to claim 1, or a pharmaceutically acceptable salt thereof, wherein $R^3$ is Cl or Br.

4. The compound according to claim 1, or a pharmaceutically acceptable salt thereof, wherein $R^4$ is $R^aR^bN$—, pyridin-4-yl, morpholin-4-yl, or

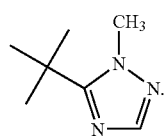

5. The compound according to claim 1, or a pharmaceutically acceptable salt thereof, wherein $R^4$ is morpholin-4-yl or

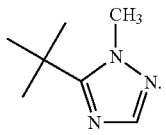

6. The compound according to claim 1, or a pharmaceutically acceptable salt thereof, wherein $R^4$ is $R^a R^b N$— and $R^a$ and $R^b$ are independently $C_1$-$C_3$alkyl.

7. The compound according to claim 1, or a pharmaceutically acceptable salt thereof, which is 3-[4-bromo-2-(2-methyl-2H-[1,2,4]triazol-3-yl)-thiazol-5-yl]-2,5-dimethyl-7-(1-propyl-butyl)-pyrazolo[1,5-a]pyrimidine.

8. The compound according to claim 1, or a pharmaceutically acceptable salt thereof, which is 3-(4-bromo-2-(2-methyl-2H-[1,2,4]triazol-3-yl)-thiazol-5-yl)-7-(1-ethyl-propyl)-2,5-dimethyl-pyrazolo[1,5-a]pyrimidine.

9. The compound according to claim 1, or a pharmaceutically acceptable salt thereof, which is 3-(4-chloro-2-morpholin-4-yl-thiazol-5-yl)-7-(1-ethyl-propyl)-2,5-dimethyl-pyrazolo[1,5-a]pyrimidine.

10. A pharmaceutical composition comprising: a compound according to claim 1, or a pharmaceutically acceptable salt thereof, and a pharmaceutically acceptable excipient.

\* \* \* \* \*